(12) United States Patent
Kataoka et al.

(10) Patent No.: US 8,791,086 B2
(45) Date of Patent: Jul. 29, 2014

(54) POLYION COMPLEX COMPRISING PHD2 EXPRESSION INHIBITING SUBSTANCE

(75) Inventors: Kazunori Kataoka, Tokyo (JP); Shourong Wu, Tokyo (JP); Nobuhiro Nishiyama, Tokyo (JP); Keiji Itaka, Tokyo (JP); Hiroyuki Koyama, Tokyo (JP); Takuya Hashimoto, Tokyo (JP); Yuichi Tei, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 13/386,154

(22) PCT Filed: Jul. 22, 2010

(86) PCT No.: PCT/JP2010/062344
§ 371 (c)(1),
(2), (4) Date: Mar. 28, 2012

(87) PCT Pub. No.: WO2011/010691
PCT Pub. Date: Jan. 27, 2011

(65) Prior Publication Data
US 2012/0177594 A1    Jul. 12, 2012

(30) Foreign Application Priority Data
Jul. 22, 2009    (JP) ................................. 2009-171562

(51) Int. Cl.
*A01N 43/04*    (2006.01)
*C07H 21/04*    (2006.01)
*C12N 15/87*    (2006.01)

(52) U.S. Cl.
USPC .......... 514/44; 435/6.1; 435/91.1; 435/91.31; 435/455; 525/54.2; 536/23.1; 536/24.5

(58) Field of Classification Search
USPC ......... 435/6.1, 91.1, 91.31, 455; 514/1, 2, 44; 536/23.1, 24.5; 525/54.2
See application file for complete search history.

(56) References Cited

U.S. PATENT DOCUMENTS

| | | | |
|---|---|---|---|
| 7,780,957 B2 | 8/2010 | Kataoka et al. | |
| 7,829,657 B2 | 11/2010 | Kataoka et al. | |
| 2001/0000510 A1 | 4/2001 | Sakurai et al. | |
| 2002/0082198 A1 | 6/2002 | Sakurai et al. | |
| 2006/0025330 A1 | 2/2006 | Sakurai et al. | |
| 2007/0059271 A1 | 3/2007 | Kataoka et al. | |
| 2008/0249049 A1 | 10/2008 | Kataoka et al. | |
| 2009/0258416 A1 | 10/2009 | Kataoka et al. | |
| 2010/0137512 A1 | 6/2010 | Kataoka et al. | |
| 2011/0076319 A1* | 3/2011 | Orlowski et al. | 424/426 |
| 2011/0195899 A1* | 8/2011 | Hays Putnam et al. | 514/11.4 |
| 2011/0223255 A1* | 9/2011 | Thiesen et al. | 424/489 |
| 2013/0116405 A1* | 5/2013 | Yu et al. | 530/324 |

FOREIGN PATENT DOCUMENTS

| | | |
|---|---|---|
| JP | 8-188541 | 7/1996 |
| JP | 2003-169688 | 6/2003 |
| JP | 2003-528131 | 9/2003 |
| JP | 2004-352972 | 12/2004 |
| JP | 2005-82557 | 3/2005 |
| WO | 01/72283 | 10/2001 |
| WO | 2005/078084 | 8/2005 |
| WO | 2006/085664 | 8/2006 |
| WO | 2007/099660 | 9/2007 |
| WO | WO 2007111333 | * 10/2007 |
| WO | 2008/062909 | 5/2008 |

OTHER PUBLICATIONS

Mazzone et al., Cell, vol. 136, pp. 839-851 (Mar. 2009).*
Wu et al., Molecular Therapy, vol. 16, No. 7, pp. 1227-1234 (2008).*
Katoaka et al, Nucleic Acids Symp. Series, No. 49, pp. 17-18 (2005).*
Han et al, Molecular Therapy, vol. 17, No. 8, pp. 1404-1410 (2009).*
International Search Report and Written Opinion issued Sep. 14, 2010 in International (PCT) Application No. PCT/JP2010/062344.
A. K. Olsson et al., "VEGF Receptor Signalling—in Control of Vascular Function", Nature Reviews Molecular Cell Biology, vol. 7, pp. 359-371, 2006.
M. Shibuya et al., "Signal Transduction by VEGF Receptors in Regulation of Angiogenesis and Lymphangiogenesis", Experimental Cell Research, vol. 312, pp. 549-560, 2006.
P. Magnusson et al., "Deregulation of Flk-1/Vascular Endothelial Growth Factor Receptor-2 in Fibroblast Growth Factor Receptor-1-Deficient Vascular Stem Cell Development", Journal of Cell Science, vol. 117, pp. 1513-1521, 2004.
M. Detmar et al., "Increased Microvascular Density and Enhanced Leukocyte Rolling and Adhesion in the Skin of VEGF Transgenic Mice", J. Invest. Dermatol., vol. 111, pp. 1-6, 1998.
H. Lee et al., "Maintenance of Vascular Integrity in the Embryo Requires Signaling Through the Fibroblast Growth Factor Receptor", The Journal of Biological Chemistry, vol. 275, No. 43, pp. 33679-33687, 2000.
M. Simons et al., "Pharmacological Treatment of Coronary Artery Disease with Recombinant Fibroblast Growth Factor-2: Double-Blind, Randomized, Controlled Clinical Trial", Circulation, vol. 105, pp. 788-793, 2002.

(Continued)

*Primary Examiner* — Jane Zara

(74) *Attorney, Agent, or Firm* — Wenderoth, Lind & Ponack, L.L.P.

(57) ABSTRACT

The present invention aims to provide a gene delivery system with higher safety and higher sustainability, which is effective for the treatment of ischemic diseases and the like, and the like. The present invention provides a pharmaceutical composition containing, as an active ingredient, a polyanionic substance that suppresses expression of PHD2, and containing a polyion complex of the polyanionic substance and a polycation chargeable polymer.

9 Claims, 7 Drawing Sheets

(56) References Cited

OTHER PUBLICATIONS

D. Henry et al., "The VIVA Trial: Vascular Endothelial Growth Factor in Ischemia for Vascular Angiogenesis", Circulation, vol. 107, pp. 1359-1365, 2003.

R. J. Lederman et al., "Therapeutic Angiogenesis with Recombinant Fibroblast Growth Factor-2 for Intermittent Claudication (the TRAFFIC Study): A Randomised Trial", The Lancet, vol. 359, pp. 2053-2058, Jun. 15, 2002.

M. S. Pepper et al., "Potent Synergism Between Vascular Endothelial Growth Factor and Basic Fibroblast Growth Factor in the Induction of Angiogenesis in Vitro", Biochemical and Biophysical Research Communications, vol. 189, No. 2, pp. 824-831, Dec. 15, 1992.

T. Asahara et al., "Synergistic Effect of Vascular Endothelial Growth Factor and Basis Fibroblast Growth Factor on Angiogenesis In Vivo", Circulation, vol. 92, pp. 365-371, 1995.

M. R. Kano et al., "VEGF-A and FGF-2 Synergistically Promote Neoangiogenesis Through Enhancement of Endogenous PDGF-B-PDGFRβ Signaling ", Journal of Cell Science, vol. 11, pp. 3759-3768, May 10, 2005.

T. P. Richardson et al., "Polymeric System for Dual Growth Factor Delivery", Nat. Biotechnol., vol. 19, pp. 1029-1034, Nov. 2001.

R. Cao et al., "Angiogenic Synergism, Vascular Stability and Improvement of Hind-Limb Ischemia by a Combination of PDGF-BB and FGF-2", Nature Medicine, vol. 9, No. 5, pp. 604-613, May 2003.

M. Mazzone et al., "Heterozygous Deficiency of *PHD2* Restores Tumor Oxygenation and Inhibits Metastasis Via Endothelial Normalization", Cell, vol. 136, pp. 839-851, Mar. 6, 2009.

S. Wu et al., "Enhancement of Angiogenesis Through Stabilization of Hypoxia-Inducible Factor-1 by Silencing Prolyl Hydroxylase Domain-2 Gene", The American Society of Gene Therapy, Molecular Therapy, vol. 16, No. 7, pp. 1227-1234, Jul. 2008.

K. Kataoka et al., "Smart Polymeric Micelles as Nanocarriers for Oligonucleotides and siRNA Delivery", Nucleic Acids Symposium Series, No. 49, pp. 17-18, 2005.

Peter Fraisl et al , "Inhibition of oxygen sensors as a therapuetic strategy for ischaemic and inflammatory disease", Nature Reviews, Drug Discovery, pp. 139-152, 2009, vol. 8.

Peter Fraisl et al., "Regulation of Angiogenesis by Oxygen and Metabolism", Developmental Cell, vol. 16, pp. 167-179, 2009.

Japanese Office Action, with English translation, mailed Sep. 10, 2013 in corresponding Japanese Application No. 2009-171562.

\* cited by examiner

```
                            SEQUENCE LISTING

<160> NUMBER OF SEQ ID NOS: 14

<210> SEQ ID NO 1
<211> LENGTH: 7102
<212> TYPE: DNA
<213> ORGANISM: Homo sapiens

<400> SEQUENCE: 1
ttaggggcag aaaaacattt gtaataatta atggctttga gagacacaag gctttgtttg      60
ccccagagta ttagttaacc cacctagtgc tcctaatcat acaatattaa ggattgggag     120
ggacattcat tgcctcactc tctatttgtt tcaccttctg taaaattggt agaataatag     180
tacccacttc atagcattgt atgatgatta aattggttaa tatttttaaa atgcttagaa     240
cacagattgg gcacataaca gcaagcacca catgtgttta taagataaat tcctttgtgt     300
tgccttccgt taaagtttaa ataagtaaat aaataaataa atacttgcat gacattttga     360
agtctctcta taacatctga gtaagtggcg gctgcgacaa tgctactgga gttccagaat     420
cgtgttggtg acaagattgt tcaccagcat atggtgtggt gaaaactcac taatttggaa     480
ttagttcaga ttattaagcc tgaataggtg aaaatcctga aatcaaggat ctttggaact     540
atttgaaatc agtattttat attttcctgt tgtattcatt aaagtgttgc aagtgttcta     600
tttgatggat taagtatatt taggatatac atgttcaatt tgtgattttg tatacttaat     660
tggaacaaga aagctaataa aggttttgat atggacatct attctttttaa gtaaacttca     720 atgaaaatat atgagtagag catatagaga tgtaaataat ttgtggacac accacagact     780
gaaatagcaa atttaaaaga aattgttgga agaatcaagt gtttgtggaa tgagtcctcc     840
tagtaaagtt cctgctcttg tgaataatta agcctcatgt ataattacta tagcaaaagg     900
aagcctaaga agtattagac tctacttgta tttaaattac atttacata atttatgtgt     960 atgaaaaatg ttttaaatgc ttattttcgt aagccatgag atagctcctt tatatttttaa    1020 gaatttctga attaatttgc ttggatttta ttagtgcaaa tggcagagct agcaattcct    1080
ttttctgtgt tcccattcca tcctattcat ccctctttta ggaaactctg aactctggat    1140
tgtccttgtt tacatacctg cctcctgcat tggactatgt gtctctgagt gtagtatgac    1200
taattcattt gtttgtcaag gactctcaat gcatttgttg aacagcctaa ttagtaatgt    1260
ctgcaacaat gacattttac tgtatttaat aaagctctgg gaaagtagga tacacataag    1320
acaggtctag gtctaaattc tttacagaaa cttggatttt tagttcggtt tgaaatttga    1380
agatgtgagt atatttatct cagtttccca aaggacaagc taattggaat tatcatcctc    1440
tttcacttga ttggatcccc agaatgccat ttacgcatgc agcaggattt tataacagtt    1500
ttaaattctg tatatttgat gaagaggttt tatattttg gattcaagcc tcttttttaaa    1560 cttctacaat atggtttaca ataattcctt atatcctgct tttgaaatac atattacaac    1620 ttttaagtt tggaaggcta tatttcaagg actgaagtta cagtatactc aagtgataca    1680
caagcctagc acccccacttt ccacatagtg ttcgataaag attgataaac tcgaaatcac    1740
agacctttta attcttaaga caaatagcag cagaaagaaa catctttggc ttatttctgg    1800
taaggttttt atgctctgta aaacaaagaa ttgtattcat ccgcgcagca cagattctat    1860
```

```
taaaaataaa tgtgagagtc gttaatgtag tactgctcat ttaccatcaa aattcacttt    1920
tcaggaataa tcccatcagt ttaaattgga tattggaatg agcattgatt acatttaact    1980
tggtagccca aaatttcttc atggggtttt gaactcggcg ggatttcaaa ggttttaaaa    2040
atgagttttt gattttttt aaaaccctca aatttcatta cctttaaact aggtcgaaac     2100
ggggcgcaag agattggatt aacaccatag taatacttat tttgttctta accatttcag    2160
ggcttcttga aatagaggct gtatggtgta atggaaaaaa cagccttgga atctgggagc    2220
ctgattcctg gattcagtcc cagttttgcg tgaccttggg caagttactt tacttctctg    2280
aatttccgtt tcctcctctg caaaatgagg atcgcaatag ccaccttgca accttgactg    2340
gagcgagcct cgcacacccc gcgccggcct ggaggaagag cagccatgat tacgccgcct    2400
tcgctccgct acccgcttgc ggctggcgcc ctcctccagc aggtgtaggc gctgccgcgc    2460
tgccccacgc ctttccgccg ctcgcgggcc tgcgcctcgg cgtccccgag gaggccgctg    2520
cgggctgagg tagcgcaccg gcctctcggc gtcccagtcc ggtcccgggc ggagggaaag    2580
cgggcgaccc acctccgagg cagaagccga ggcccggccc cgccgagtgc ggaggagcgc    2640
aggcagcccc cgcccctcgg ccctcccccc ggccctcccg gccctccctc cgcccccctcc    2700 gccctcgcgc gccgcccgcc cgggtcgccg cggggccgtg gtgtacgtgc agagcgcgca    2760
gagcgagtgg cgcccgtatg ccctgcgctc ctccacagcc tgggccgggc cgcccgggac    2820
gctgaggcgg cggcggcggc cgaggggggcc ggtcttgcgc tccccaggcc cgcgcgcctg    2880
agcccaggtt gccattcgcc gcacaggccc tattctctca gccctcggcg gcgatgaggc    2940
gctgaggcgg ctgccggcgc tgcgccggag cttaggactc ggaagcggcc gggccgaggg    3000
cgtggggtgc cggcctccct gaggcgaggg tagcgggtgc atggcgcagt aacggcccct    3060
atctctctcc ccgctcccca gcctcgggcg aggccgtccg gccgctaccc ctcctgctcg    3120
gccgccgcag tcgccgtcgc cgccgccgcc gccgccatgg ccaatgacag cggcgggccc    3180
ggcgggccga gcccgagcga gcgagaccgg cagtactgcg agctgtgcgg aagatggag     3240 aacctgctgc gctgcagccg ctgccgcagc tccttctact gctgcaagga gcaccagcgt    3300
caggactgga agaagcacaa gctcgtgtgc caggggcagca agggcgccct cggccacgga    3360
gtgggcccac accagcattc cggccccgcg ccgccggctg cagtgccgcc gcccagggcc    3420
ggggcccggg agcccaggaa ggcagcggcg cgccgggaca acgcctccgg ggacgcggcc    3480
aagggaaaag taaggccaa gccccggcc gacccagcgg cggccgcgtc gccgtgtcgt      3540
gcggccgccg gcgccagggg ctcggcggtg gctgccgaag ccgagcccgg caaggaggag    3600
ccgccggccc gctcatcgct gttccaggag aaggcgaacc tgtaccccccc aagcaacacg    3660 cccggggatg cgctgagccc cggcggcggc ctgcggccca acgggcagac gaagcccctg    3720
ccggcgctga agctggcgct cgagtacatc gtgccgtgca tgaacaagca cggcatctgt    3780
gtggtggacg acttcctcgg caaggagacc ggacagcaga tcgcgacga ggtgcgcgcc     3840 ctgcacgaca ccgggaagtt cacggacggg cagctggtca gccagaagag tgactcgtcc    3900
aaggacatcc gaggcgataa gatcacctgg atcgagggca aggagcccgg ctgcgaaacc    3960
attgggctgc tcatgagcag catggacgac ctgatacgcc actgtaacgg gaagctgggc    4020
agctacaaaa tcaatggccg gacgaaagcc atggttgctt gttatccggg caatggaacg    4080
ggttatgtac gtcatgttga taatccaaat ggagatggaa gatgtgtgac atgtatatat    4140
tatcttaata aagactggga tgccaaggta agtggaggta tacttcgaat ttttccagaa    4200
```

```
ggcaaagccc agtttgctga cattgaaccc aaatttgata gactgctgtt tttctggtct    4260
gaccgtcgca accctcatga agtcaacca gcatatgcta caaggtacgc aataactgtt    4320
tggtatttg  atgcagatga gagagcacga gctaaagtaa aatatctaac aggtgaaaaa    4380
ggtgtgaggg ttgaactcaa taaaccttca gattcggtcg gtaaagacgt cttctagagc    4440
ctttgatcca gcaataccc  acttcaccta caatattgtt aactatttgt taacttgtga    4500
atacgaataa atgggataaa gaaaaataga caaccagttc gcattttaat aaggaaacag    4560
aaacaacttt tgtgttgca  tcaaacagaa gattttgact gctgtgactt tgtactgcat    4620
gatcaacttc aaatctgtga ttgcttacag gaggaagata agctactaat tgaaaatggt    4680
ttttacatct ggatatgaaa aagtgccct  gtgtagaatt ttttcattc  ttatattttg    4740
ccagatctgt tatctagctg agttcatttc atctctccct tttttatatc aagtttgaat    4800
ttgggataat ttttctatat taggtacaat ttatctaaac tgaattgaga aaaaattaca    4860
gtattattcc tcaaaataac atcaatctat ttttgtaaac ctgttcatac tattaaattt    4920
tgccctaaaa gacctcttaa taatgattgt tgccagtgac tgatgattaa ttttatttta    4980
cttaaaataa gaaaggagc  actttaatta caactgaaaa atcagattgt tttgtagtcc    5040
ttccttacac taatttgaac tgttaaagat tgctgctttt tttttgacat tgtcaataac    5100
gaaacctaat tgtaaaacag tcaccattta ctaccaataa cttttagtta atgttttaca    5160
aggaaaaaga cacaagaaga gtttaaattt tttttgtttg ttttgttttt ttgagacagt    5220
cttgctctgt tacccaggct ggaggggagt ggtgcattct tggctcactg caacctccgc    5280
ctcccaggtt caagcaatcc tcccacctca gcctcccaac tagctgggac tgcaggcaca    5340
caccaccatg cctgactaat ttttgtatgt ttagtagaga cggggttttg ccatgttgcc    5400
taggctgggt tttaagttaa atttttttaaa aaactaaagt gactggcact aagtgaactt    5460
gagattatcc tcagcttcaa gttcctaaga taagggcttt cttaagcttt caggtgtatg    5520
tatcctctag atgtagacaa taatgtccca tttctaagtc ttttccttt  gcttctcctt    5580
aaattgattg tacttccaaa tttgctgtta tgtttttttc ctaatactgt gatctatctg    5640
atctgcagac aagaaccttg tctctgttga agagcatcaa ggggagatta tgtacacatt    5700
gaaactgaag tgtggtgtta ctgacggaat gtgcagtaac tcctcagata tctgttaagg    5760
catttcccag atgtgatgcc agccttctta cctgtactga agatgcttaa gcttagaaaa    5820
aaacaaaaca gatgcaaaat cagataattt tattttgttt catgggtttt cttatttact    5880
ttttaaacaa ggaaggaata ttagaaaatc acacaaggcc tcacatacat gttatttaaa    5940
gaatgaattg ggacggatgt cttagacttc actttcctag gcttttagc  aaaacctaaa    6000
gggtggtatc catattttgc gtgaattatg ggtgtaagac cttgcccact taggtttttct   6060
atctctgtcc ttgatcttct ttgccaaaat gtgagtatac agaaattttc tgtatatttc    6120
aacttaagac attttttagca tctgtatagt ttgtattcaa tttgagacct tttctatggg   6180
aagctcagta atttttattta aaagattgcc attgctattc atgtaaaaca tggaaaaaa    6240
ttgtgtagtg aagccaacag tggacttagg atgggattga atgttcagta tagtgatctc    6300
acttaggaga atttgcagga gaaagtgata gtttattgtt ttttcctcgc ccatattcag    6360
ttttgttcta cttcctcccc ttccttccag atgataacat cacatctcta cagtaagtgc    6420
ctctgccagc ccaacccagg agcgcaagtt gtctttgcca tctggtctat agtacagtgc    6480
gcggcgttag gccacaactc aaaagcatta tcttttttag ggttagtaga aattgtttta    6540
tgttgatggg aggtttgttt gattgtcaaa atgtacagcc acagccttt  aatttgggag    6600
```

```
ccctgttgt cattcaaatg tgtacctcta cagttgtaaa aagtattaga ttctactatc    6660
tgtgggttgt gcttgccaga caggtcttaa attgtatatt ttttggaaaa gtttatatac    6720
tctcttagga atcattgtga aaagatcaag aaatcaggat ggccatttat ttaatatcca    6780
ttcatttcat gttagtggga ctattaactt gtcaccaagc aggactctat ttcaaacaaa    6840
atttaaaact gtttgtggcc tatatgtgtt taatcctggt taaagataaa gcttcataat    6900
gctgttttta ttcaacacat taaccagctg taaaacacag acctttatca agagtaggca    6960
aagattttca ggattcatat acagatagac tataaagtca tgtaatttga aaagcagtgt    7020
ttcattatga aagagctctc aagttgcttg taaagctaat ctaattaaaa agatgtataa    7080
atgttgttga aacattaaaa aa                                            7102
```

```
<210> SEQ ID NO 2
<211> LENGTH: 3524
<212> TYPE: DNA
<213> ORGANISM: Mus musculus

<400> SEQUENCE: 2
ggctgggccc gccgcccag ggcgctgtgc gccgcgcagg ccgcgctctc tccggcgcga      60
tgcggcgcta ggcggccccg ggcaaggcag gcgaggccag ggcgcgcgcg gcctcccgca    120
gcgggcggcg gccccgggcg ggcgccccga cggccccgcc gccgcccgc tcccggcccg     180 cggcccgccc tgccgcggcc atggccagtg acagcggcgg gccggcgtg ctgagcgcca     240 gcgagcgcga ccggcagtac tgcgagctgt gcgggaagat ggagaacctg ctgcgctgcg    300
gccgctgccg cagctccttc tactgctgca aagagcacca gcgccaggac tggaagaagc    360
acaagctggt gtgccaggg ggcgaggccc ccgcgcgca gcccgcgccg gcgcagcccc      420
gcgtcgcgcc cccgcccggt ggggccccg gagccgcgcg cgccggcggg gcggcccggc     480
gcggggacag cgcggcggcc tcgcgcgtac cgggcccgga ggacgcggcg caggcccgga    540 gcggcccccgg cccagcagag cccggctccg aggatcctcc gcttagccgg tctccgggcc    600
ccgagcgcgc cagcctgtgc ccagcggggtg gcggccccgg ggaggcgctg agtcccggtg    660
gagggctgcg gcccaacggg cagaccaagc cgttgcccgc gttgaagctg gctctggagt    720
acatcgtgcc gtgcatgaac aagcacggca tctgcgtggt ggacgacttc ctgggcaggg    780
agaccgggca gcagatcggc gatgaggtgc gcgccctgca cgacaccggc aagttcacgg    840
acgggcagct ggtcagccag aagagtgact cttccaagga catccgggg gaccagatca     900 cctggatcga gggcaaagag cccggctgcg aaaccatcgg cctgctcatg agcagcatgg    960
acgacctgat ccgccactgc agcgggaagc tgggcaacta caggataaac ggccgaacga   1020
aagccatggt tgcttgttac ccaggcaacg gaacaggcta tgtccgtcac gttgataacc   1080 caaatgggaga tggaagatgc gtgacatgta tatattatct aaataaagac tgggacgcca   1140
aggtaagtgg aggtattctt cgaatttttc cagaaggcaa agcccagttt gctgacattg   1200 aacccaaaatt tgatagactg ctgttttttct ggtctgaccg gcgtaaccct catgaagtac   1260
agccagcata cgccacaagg tacgcaataa ctgtttggta ttttgatgca gatgagcgag    1320
cgagagctaa agtaaaatat ctaacaggtg agaaggtgt gagggttgaa ctcaagccca     1380
attcagtcag caaagacgtc tagtggggcc ttgggtccgg cagtacccac gtcacctaca    1440
gcctctcagt tgccttctgt ggactcgtgg acaggatgga cagagagaca cctgcctggt    1500
atttcagctg ggagccaggc gacttcgccg ggtgtcatcc aacagagggc tccatctgct    1560
```

| | |
|---|---|
| gggactgtac tgtggggtca gctccagatc tgtgactgct cttggctgct gacccaagag | 1620 |
| gagacgctgt cggaggagag tagcttttcc atctggacac gaaacaaggg cccttttgtag | 1680 |
| gaatttcttc agtcttctat tttgccagac ctgtcaccta actgagttca tttcatctct | 1740 |
| tttttatatc aagttttgaa ttcggggaat ttttgtatta ggtacaattt atcaaaactg | 1800 |
| aattaagaaa aaaaaattta cagtattatt ctcaaaataa catcaatcta tttttgtaaa | 1860 |
| cctcttcatg ctattaaatt ttgccctcaa ggcctcctgc gatgattgtt gccagtgagt | 1920 |
| gacgacgtgt tgcttctgcc tgaacgtaaa ggacgggcgg gcgctgtgtc ccagcccgag | 1980 |
| tgcacgaggt ttttcttggc ccgtctctca gtgattccaa cctgtaaagg tcactgctct | 2040 |
| cgcgcttcga ccgacctaac agtagatggt tgccactggc actcaactaa ctcaacatag | 2100 |
| ttacaagagg aaacaagcca caggagaggg tttgtctctt cagttaattt ttttaaagcg | 2160 |
| aagtgacggg cactaaatga actcggggct ctccctcagc ttcgggttcc tgagacaaag | 2220 |
| ggctttcttc tgcggcaggt ctagcctgcc tacagccgtg tcccactgcc gcaggtttcc | 2280 |
| ttgtggcttc tccgtagttt tgactgtgct tccagaccct tccaggtcag ggctgtgttc | 2340 |
| ttgtggcagg gcacctggtg gacccaggca cgtgaatgtg gtatgtggtt gtagcctcaa | 2400 |
| tcgtggccat cggctccttg gacagccacg agccattttc atacccaata atgaaagctg | 2460 |
| tgtgctagct tagaaatcaa aggggtgta aaagcacaca ttctttgttt tatgggtttt | 2520 |
| tctctttta gaggacagag ggacaaccac acgaggctgc cagactcctg tcacctctac | 2580 |
| agtccccta gaaagccaga gtttgcacag attgtgggta taactcctgt cccttaggt | 2640 |
| gttctatctc cgaccttgat ctttgccaaa atgtgtgtat gcagaactat ttctgtgtat | 2700 |
| tttccttgac acccgtctta gcacctgtgt agtttgtatc cggttagaaa ccttttctat | 2760 |
| ggaaagctca gtaattctta ttaagagatt gctattgttc atgtaaaaca tgaaaacaac | 2820 |
| caagtagagc cgtgtgtgga tgagggccca ctcagcactg tgcttgcttg aggggctctc | 2880 |
| ggcaggaagt ctccttctga cccatatccg ctgaccacac ctctccagca agtgcctctg | 2940 |
| ccgctggcca gctcaaggtt tgcccacctg gccccgaagc accgtgtttc ggagttggga | 3000 |
| ggaactgttt ggcattgttg gcagaaggtg tgattgcctg gagcagcagc cttttaaatt | 3060 |
| ctggagaccc tgtagtcctt tgtatctcag acctttactg atgtaccagg tcccagattc | 3120 |
| tgtggcaggg gatggggtgg ggtgtgcttg ccagacgaaa tttaaattat ctatctttg | 3180 |
| ggaagtgtgt gctttcctgg aggtcactgt gaaaacaaac aaacaaatca ggaccgttaa | 3240 |
| ccccttaatg cccacttaaa ctcaatttca tgttaggact cttgtttaaa accatttgtg | 3300 |
| gcctgtatgt gttcatcctg gttagagaga aagctttatg acgctgtttc tgttcaacac | 3360 |
| attaaccagc tgtggaacag cccttttttgc acgacaggca gggcacttca ggattcgcag | 3420 |
| agagactcgt gtggtttgga agtggtattt cctatgaaag cctctcacgt tgcttgtaaa | 3480 |
| gctaatctaa ttaaaagat gtataaatgt tcttgaaaaa aatc | 3524 |

```
<210> SEQ ID NO 3
<211> LENGTH: 19
<212> TYPE: DNA
<213> ORGANISM: Mus musculus

<400> SEQUENCE: 3
gaactcaagc ccaattcag                                            19

<210> SEQ ID NO 4
<211> LENGTH: 19
```

<212> TYPE: DNA
<213> ORGANISM: Mus musculus

<400> SEQUENCE: 4
tgagcgagcg agagctaaa                                                   19

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
gaagctgggc aactacagga                                                  20

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
catgtcacgc atcttccatc                                                  20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
cggcgacgac ccattcgaac                                                  20

<210> SEQ ID NO 8
<211> LENGTH: 23
<212> TYPE: DNA
<213> ORGANISM: Artificial
<220> FEATURE:
<223> OTHER INFORMATION: primer

<400> SEQUENCE: 8
gaatcgaacc ctgattcccc gtc                                              23

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
gcagaagtcc catgaagtga t                                                21

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
gtctcaattg gacggcagta g                                                21

```
<210> SEQ ID NO 11
<211> LENGTH: 23
<212> TYPE: DNA
<213> ORGANISM: Artificial
<220> FEATURE:
<223> OTHER INFORMATION: primer

<400> SEQUENCE: 11
gtcacggaaa tactccagtt ggt                                              23

<210> SEQ ID NO 12
<211> LENGTH: 19
<212> TYPE: DNA
<213> ORGANISM: Artificial
<220> FEATURE:
<223> OTHER INFORMATION: primer

<400> SEQUENCE: 12
cccgttttgg atccgagtt                                                   19

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13
ttgtgattct ggtgattgtg g                                                21

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
cttgtttcgc tttatttttg t                                                21
```

POLYION COMPLEX COMPRISING PHD2 EXPRESSION INHIBITING SUBSTANCE

This application is a U.S. national stage of International Application No. PCT/JP2010/062344 filed Jul. 22, 2010.

The present invention relates to a polyion complex comprising a PHD2 expression suppressing substance. More particularly, the present invention relates to the field of treatment of ischemic diseases and the like, which uses a polyanionic substance that suppresses expression of PHD2 and a polycation chargeable polymer.

BACKGROUND ART

Angiogenesis treatment for ischemic diseases is intended to enhance neovascularization by delivering vascularization factors such as vascular endothelial growth factor (VEGF) and fibroblast growth factor 2 (FGF2), or DNA vectors that encode these proteins, to ischemized tissue (Non-patent Documents 1 to 3). VEGF is produced in the initial stage of the angiogenesis cascade and involved in the initial activation of endothelial cells, hence said to be an important factor of vascular development. It has been reported that in the skin of VEGF-transgenic mice, a very large number of blood vessels exhibiting excess permeabiity are formed (Non-patent Document 4). FGF2 has been reported to act as a mitogen on both endothelial cells and wall cells, and the role thereof in angiogenesis has also been identified (Non-patent Documents 3 and 5). As stated above, a very large number of studies have been conducted on vascularization therapies using VEGF or FGF2 alone.

In clinical studies, the safety of VEGF and FGF2 in delivery is demonstrated at the stage of phase I, but no expected efficacy has been demonstrated in phase II (Non-patent Documents 6 to 8). As a result, it has been suggested that to induce functional blood vessels, it is unsatisfactory to administer a single vascularization factor alone.

Later, research into vascularization therapy became focused on administering vascularization factors in combination. Specifically, a combination of VEGF and FGF2, or a combination of VEGF or FGF2 and another vascularization factor like angiopoietin 1 (Ang-1) or platelet-derived growth factor-BB (PDGF-BB), has been reported to have synergistic action effective in neovascularization in in vitro and in vivo experiments (Non-patent Documents 9 to 13). These results demonstrate the complexity of the mechanism for vascularization involving the temporarily and spatially integrated expression of a large number of vascularization factors. Constructing functional blood vessels requires three complex processes, i.e., vasculogenesis, angiogenesis, and arteriogenesis; however, because no vascularization factors that act on all these processes in common are currently available, a single vascularization factor alone is inadequately effective, and it is thought that a satisfactory effect is difficult to obtain even when several kinds of vascularization factors are combined. Furthermore, in current clinical studies using a gene of vascularization factor and the like, methods of administration by intramuscular injection are employed; however, because intramuscular injection is highly invasive to tissue, and also because its gene transfer effect is regionally limited so that the transfer efficiency is not always satisfactory, it seems to be necessary to improve the method of administering a vascularization factor.

While there is a need for discovering a radical factor that acts on all angiogenesis processes and developing countermeasures, what can become a key thereto is hypoxia-inducible factor (HIF). Known members of the HIF family include HIF-1, HIF-2, HIF-3 and the like. HIF-1 is a hetero-dimer consisting of an α subunit and a β subunit, functioning as a pivotal regulatory factor for oxygen homeostasis. It is known that the production of vascularization factors such as VEGF, FGF2, and Ang-1 is induced directly or indirectly by the α subunit of HIF-1 (HIF-1α). In the presence of oxygen, however, HIF-1α is hydroxylated by prolyl hydroxylase domain-2 (PHD2); the hydroxylated HIF-1α is then decomposed by E3 ubiquitin ligase complex. In a study using PHD2-hetero-deficient mice, it was shown that tumor metastasis is suppressed via normalization of vascular endothelium, suggesting that inhibiting PHD2 leads to cancer treatment (Non-patent. Document 14).

The present inventors attempted to introduce a PHD2-siRNA expression plasmid into mouse fibroblasts to achieve silencing of the PHD2 gene, and reported that the expression of VEGF and FGF2 was significantly induced, and that angiogenesis was induced when the introduced cells were subcutaneously transplanted to mice (Non-patent Document 15).

Meanwhile, the present inventors reported that a polyion complex of a nucleic acid and a block copolymer is useful as a delivery system for nucleic acids such as DNA (Patent Documents 1 to 5). However, no delivery system for nucleic acids is known to be effective in the treatment of ischemic diseases.

DOCUMENT LIST

Patent Documents patent document 1: JP-A-8-188541
patent document 2: JP-A-2004-352972
patent document 3: WO2005/078084
patent document 4: WO2006/085664
patent document 5: WO2007/099660

Non-patent Document non-patent document 1: Olsson A K et al., Nat Rev Mol Cell Biol 7: 359-371, 2006
non-patent document 2: Shibuya M et al., Exp Cell Res 312: 549-560, 2006
non-patent document 3: Magnusson P et al., J Cell Sci 117: 1513-1523, 2004
non-patent document 4: Detmer M et al., J Invest Dermatol 111: 1-6, 1998
non-patent document 5: Lee S H et al., J Biol Chem 275: 33679 33687, 2000
non-patent document 6: Simons M et al., Circulation 105: 788-793, 2002
non-patent document 7: Henry T D et al., Circulation 107: 1359-1365, 2003
non-patent document 8: Lederman R J et al., Lancet 359: 2053-2058, 2002
non-patent document 9: Pepper M S et al., Biochem Biophys Res Commun 189: 824-831, 1992
non-patent document 10: Asahara T et al., Circulation 92: 11365-11371, 1995
non-patent document 11: Kano M R et al., J Cell Sci 118: 3759-3768, 2005
non-patent document 12: Richardson T P et al., Nat Biotechnol 19: 1029-1034, 2001
non-patent document 13: Cao R et al., Nat Med 9: 604-613, 2003
non-patent document 14: Mazzone M et al., Cell 136: 839-851, 2009 non-patent document 15: Wu S et al., Mol Ther 16: 1227-1234, 2008

SUMMARY OF THE INVENTION

Problems to be Solved by the Invention

The present invention has been made in view of the above-mentioned problems, and aims to provide a gene delivery system effective for the treatment of ischemic diseases and the like, which has higher safety and higher sustainability, and the like.

Means of Solving the Problems

The present inventors conducted extensive investigations to solve the above-described problems, and, as a result, taking note of the fact that a PHD2 expression suppressing substance with a nucleic acid as an ingredient is polyanionic, found that the expression suppressing substance can be transported to target tissue while in a stable state by using a polyion complex of the expression suppressing substance and a polycation chargeable polymer having a particular structure or a ternary system complex of the polyion complex and glycosaminoglycan. Furthermore, the present inventors succeeded in allowing a vascularization effect to be exhibited over a wide area of recipient tissue in a living organism, and allowing the effect to persist for a long time, by using the polyion complex or ternary system complex, and have developed the present invention.

Accordingly, the present invention provides the following.

(1) A pharmaceutical composition comprising, as an active ingredient, a polyanionic substance that suppresses the expression of PHD2, and comprising a polyion complex of the polyanionic substance and a polycation chargeable polymer.

(2) The pharmaceutical composition of (1), wherein the polyanionic substance is RNAi inducing nucleic acid against PHD2, antisense nucleic acid against PHD2 or ribozyme against PHD2 or an expression vector thereof.

(3) The pharmaceutical composition of (2), wherein the RNAi inducing nucleic acid is siRNA or an expression vector thereof.

(4) The pharmaceutical composition of any of (1)-(3), wherein the polycation chargeable polymer is a polymer having a main chain with polypeptide, polysaccharide, polyester, polyether, polyurethane or vinyl polymer as a base, and, as a side chain, a segment chain derived from a chargeable polymer comprising a group represented by the formula —NH—$(CH_2)_a$—$(NH(CH_2)_2)_e$—$NH_2$ (wherein a and e are each independently an integer of 1-5) bonded directly or via a linking group to said main chain.

(5) The pharmaceutical composition of (4), wherein the polycation chargeable polymer is a block copolymer having a segment chain derived from the aforementioned chargeable polymer and a segment chain derived from a non-ionic hydrophilic polymer.

(6) The pharmaceutical composition of (5), wherein the non-ionic hydrophilic polymer is selected from the group consisting of poly(ethylene glycol), poly(vinylalcohol), poly(vinylpyrrolidone), poly(methacrylamide), poly(acrylamide), poly(hydroxyethylmethacrylate) and poly(hydroxyethylacrylate).

(7) The pharmaceutical composition of any of (1)-(6), wherein the polycation chargeable polymer is a chargeable polymer represented by the following formula (III), a block copolymer represented by the following formula (I) or (II), or a salt thereof.

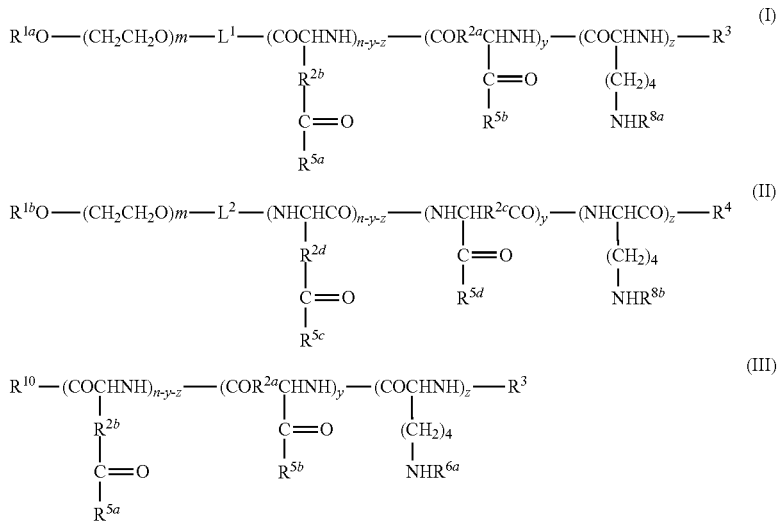

wherein, $R^{10}$ is a hydroxy group, an oxybenzyl group or an NH—$R^{11}$ group, wherein Rn is an optionally substituted straight chain or branched $C_{1-20}$ alkyl group, $R^{1a}$ and $R^{1b}$ are each independently a hydrogen atom or an optionally substituted straight chain or branched $C_{1-12}$ alkyl group, $R^{2a}$, $R^{2b}$, $R^{2c}$ and $R^{2d}$ are each independently a methylene group or an ethylene group, $R^3$ is a hydrogen atom, a protecting group, a hydrophobic group or a polymerizable group, $R^4$ is a hydroxy group, a protecting group or a group represented by —O—$X^3$, —S—$X^3$, —NH—$X^3$, or a polymerization initiator residue of polypeptide, wherein $X^3$ is a primary, secondary or tertiary amine compound, or an amine compound residue comprising one or more groups derived from a quaternary ammonium salt, or a non-amine compound residue, $R^{5a}$, $R^{5b}$, $R^{5c}$ and $R^{5d}$ are each independently a hydroxy group, an oxybenzyl group or an NH—$(CH_2)_a$—X group, wherein a is an integer of 1-5, X is each independently a primary, secondary or tertiary amine compound, or an amine compound residue comprising one or more groups derived from a quaternary ammonium salt, or a non-amine compound residue, the total of $R^{5a}$ and $R^{5b}$ or $R^{5c}$ and $R^{5d}$ contains at least two —NH—$(CH_2)_a$—$X^1$ groups (wherein $X^1$ is (NH $(CH_2)_2)_e$—$NH_2$, and e is an integer of 1-5), $R^{6a}$ and $R^{6b}$ are each independently a hydrogen atom or protecting group, wherein the protecting group is selected from the group consisting of a Z group, a Boc group, an acetyl group and a trifluoroacetyl group, $L^1$ and $L^2$ are linking groups, m is an integer of 5-20,000, n is an integer of 2-5,000, y is an integer of 0-5,000, z is an integer of 0-5,000, and y+z is not larger than n, and each repeat unit in the above-mentioned formulas is in a specified order for convenience of description; however, each repeat unit can be present at random.

(8) The pharmaceutical composition of (7), wherein X is a group selected from the group consisting of —$NH_2$, —NH—$CH_3$, —$N(CH_3)_2$ and groups represented by the following formulas:

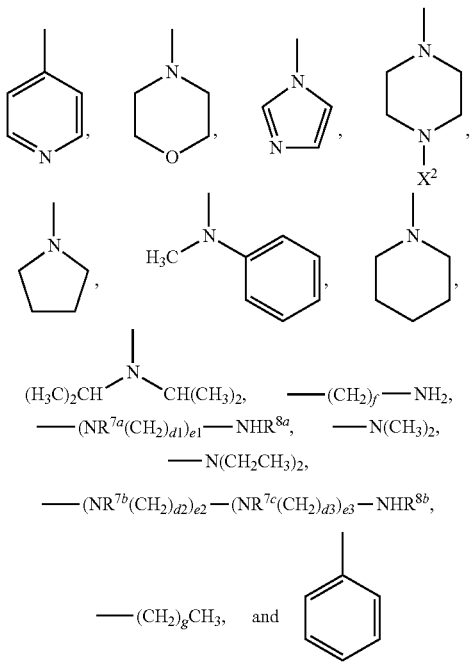

wherein, $X^2$ is a hydrogen atom, a $C_{1-6}$ alkyl group or an amino $C_{1-6}$ alkyl group, $R^{7a}$, $R^{7b}$ and $R^{7c}$ are each independently a hydrogen atom or a methyl group, d1, d2 and d3 are each independently an integer of 1-5, e1, e2 and e3 are each independently an integer of 1-5, f is an integer of 0-15, $R^{8a}$ and $R^{8b}$ are each independently a hydrogen atom or a protecting group, wherein the protecting group is selected from the group consisting of a Z group, a Boc group, an acetyl group and a trifluoroacetyl group, and g is an integer of 0-15.

(9) The pharmaceutical composition of (7) or (8), wherein $L^1$ or $L^2$ has a disulfide bond.

(10) The pharmaceutical composition of any of (1)-(9), further comprising glycosaminoglycan.

(11) The pharmaceutical composition of (10), wherein the glycosaminoglycan is chondroitin sulfate or a salt thereof.

(12) The pharmaceutical composition of any of (1)-(11), which is for the treatment or prophylaxis of an ischemic disease or artery disease.

(13) The pharmaceutical composition of (12), wherein the ischemic disease or artery disease is selected from the group consisting of ischemic cardiac disease, myocardial infarction, cardiomyopathy, angina pectoris, unstable angina pectoris, coronary sclerosis, cardiac failure, arteriosclerosis obliterans, Buerger's disease, vascular injury, artery obstruction, arterial thrombosis, organ artery obstruction, aneurysm, ischemic brain diseases, ischemic lung disease and renal infarction.

(14) A method for the treatment or prophylaxis of an ischemic disease or artery disease, comprising a step of administering the pharmaceutical composition of any of (1)-(13) to a subject in need thereof.

(15) The method for the treatment or prophylaxis of (14), wherein the ischemic disease or artery disease is selected from the group consisting of ischemic cardiac disease, myocardial infarction, cardiomyopathy, angina pectoris, unstable angina pectoris, coronary sclerosis, cardiac failure, arteriosclerosis obliterans, Buerger's disease, vascular injury, artery obstruction, arterial thrombosis, organ artery obstruction, aneurysm, ischemic brain disease, ischemic lung disease and renal infarction.

Effect of the Invention

According to the pharmaceutical composition of the present invention, it is possible to suppress the expression of PHD2, which is responsible for the proteasome degradation of HIF (HIF-1 or HIF-2) in an ordinary oxygen state, in the tissue or cells to which it is delivered, whereby the expression of a variety of HIF-induced vascularization factors (VEGF, PDGF, FGF2, Ang-1 and the like) rises directly or indirectly via stabilization of the HIF, and vascularization is promoted. The blood vessels thus formed are capable of exhibiting excellent functions based on the interactions and synergistic actions of a variety of vascularization factors, hence significantly suppressing tissue necrosis due to ischemia.

The pharmaceutical composition of the present invention is capable of delivering a polyanionic substance that suppresses the expression of PHD2 into tissue while in a stable state, whereby a vascularization effect is allowed to be exhibited over a wide area of the tissue. Furthermore, the pharmaceutical composition of the present invention is capable of persistently exhibiting the vascularization effect thereof over a long time by a single administration.

DESCRIPTION of EMBODIMENTS

Figure 1:
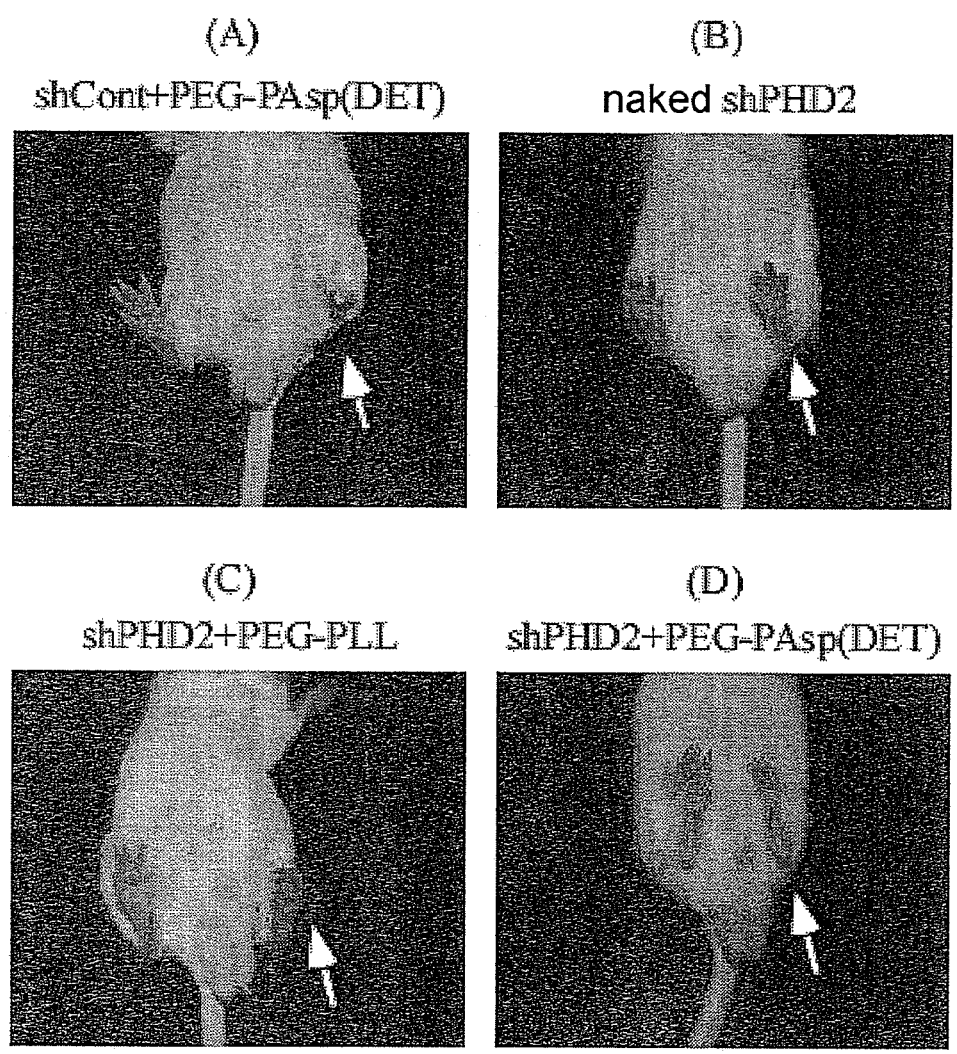
FIG. 1 shows the condition of mouse lower leg on Day 21 after ischemia treatment according to Example 1. In (A), shRNA expression plasmid (control) was administered by using a polyethylene glycol-poly(N-(2-aminoethyl)-aminoethylaspartamide) block copolymer (PEG-PAsp(DET)), in (B), shRNA expression plasmid of PHD2 was administered without using a polycation chargeable polymer, in (C), shRNA expression plasmid of PHD2 was administered by using a polyethylene glycol-polylysine block copolymer (PEG-PLL) and in (D), shRNA expression plasmid of PHD2 was administered by using PEG-PAsp (DET).

The present invention provides a pharmaceutical composition comprising, as an active ingredient, a polyanionic substance that suppresses PHD2 expression, and comprising a polyion complex of the polyanionic substance and a polycation chargeable polymer.

1. Polyanionic Substance that Suppresses the Expression of PHD2 (PHD2 Expression Suppressing Substance)

In the present invention, PHD2 (prolyl hydroxylase domain-2) is a protein belonging to the prolyl hydroxylase family. PHD2 is an enzyme possessing hypoxia-inducible factor (HIF) prolyl hydroxylase activity, particularly having the action of hydroxylating a particular proline residue in the HIF-1α molecule in an ordinary oxygen state.

In the present invention, PHD2 is a protein derived from any mammal. Examples of the mammal include human and those other than human. Examples of the mammal other than human include rodents such as mouse, rat, hamster, guinea pig and the like, experimental animals such as rabbit and the like, domestic animals such as swine, bovine, goat, horse, sheep and the like, pets such as canine, feline and the like, and primates such as monkey, orangutan, chimpanzee and the like. For use for the treatment of ischemic disease, artery disease of human, and the like, PHD2 derived from human is preferable. The base sequence and amino acid sequence of human PHD2 are known and, for example, the base sequence (SEQ ID NO: 1) (GenBank Accession No. NM_022051) and amino acid sequence of PHD2, and the like are registered in and published by GenBank. In addition, the base sequence and amino acid sequence of mouse PHD2 are known and, for example, the base sequence (SEQ ID NO: 2) (GenBank Accession No. NM_053207) and amino acid sequence of mouse PHD2, and the like are registered in and published by GenBank.

The polyanionic substance that suppresses the expression of PHD2 contained as an active ingredient in the pharmaceutical composition of the present invention is not particularly limited, as far as it is a substance that acts on the transcription process of PHD2 to suppress the expression thereof. Such suppressants include RNAi-inducing nucleic acids, antisense nucleic acids, ribozymes, or vectors for expression thereof.

The aforementioned RNAi-inducing nucleic acid refers to a polynucleotide capable of inducing RNA interference (RNAi) when introduced into a cell, and is preferably RNA or a chimera molecule of RNA and DNA. RNA interference refers to the effect of suppressing the expression of mRNA by an RNA with single-stranded or double-stranded structure comprising the same base sequence as the mRNA (or a partial sequence thereof). To obtain this RNAi effect, it is preferable to use, for example, an RNA with double-stranded structure having the same base sequence as at least 10 consecutive bases in the target mRNA (or a partial sequence thereof). However, provided that the PHD2 expression suppressing action is possessed, several bases may have been substituted, and the RNAi-inducing nucleic acid may be an RNA shorter than 10 bases long. The double-stranded structure may be composed of different strands, i.e., a sense strand and an antisense strand, and may be a double strand given by one hairpin loop (stem loop) structure of RNA (shRNA). RNAi-inducing nucleic acids include, for example, siRNAs (including shRNAs), miRNAs and the like.

It is preferable from the viewpoint of the potency of transcription suppressing activity that the RNAi-inducing nucleic acid be an siRNA. The siRNA against PHD2 can target an optionally chosen portion of the mRNA of PHD2. The siRNA molecule against PHD2 is not particularly limited, as far as an RNA interference effect is inducible; the molecule is, for example, 10 to 50 bases long, preferably 15 to 30 bases long, more preferably 20 to 27 bases long. The siRNA against PHD2 is a double strand comprising a sense strand and an antisense strand. Specifically, the siRNA against PHD2 consists of a sense strand comprising a base sequence of 10 to 50 continuous bases in the mRNA corresponding to the base sequence of SEQ ID NO:1 or 2 and an antisense strand comprising a sequence complementary thereto. The siRNA against PHD2 may have an overhang at the 5' end or 3' end of either the sense strand or the antisense strand, or both. The overhang is formed as a result of addition of one to several (for example, 1, 2 or 3) bases to an end of the sense strand and/or the antisense strand. Methods of designing an siRNA are obvious to those skilled in the art; an appropriate base sequence of siRNA can be selected from among the above-described base sequences using a variety of siRNA design softwares or algorithms.

An antisense nucleic acid against PHD2 refers to a polynucleotide that consists of a base sequence capable of hybridizing with a transcription product (mRNA or initial transcription product) of PHD2 under physiological conditions that allow the cells to express the transcription product, and that is capable of inhibiting the translation of the polypeptide encoded by the transcription product while in the hybridized state. The kind of the antisense nucleic acid may be DNA or RNA, or a DNA/RNA chimera. The antisense nucleic acid may be one having a natural type phosphoric acid diester bond, or a modified nucleotide such as of the thiophosphate type (P=O in phosphate linkage replaced with P=S), 2'-O-methyl type and the like, which are stable to decomposing enzymes. The length of the antisense nucleic acid is not particularly limited, as far as the antisense nucleic acid can hybridize specifically with a transcription product of PHD2 (for example, mRNA corresponding to the base sequence of SEQ ID NO:1 or 2); the antisense nucleic acid may be a sequence comprising a sequence complementary to about 15 bases for the shortest or to the entire sequence of the transcription product for the longest. Taking into account the issues of the ease of synthesis, antigenicity and the like, an oligonucleotide consisting of about 15 bases or more, preferably about 15 to about 30 bases, more preferably about 18 bases to about 30 bases, for example, may be mentioned. Furthermore, the antisense nucleic acid may be one capable of not only hybridizing with a transcription product of PHD2 to inhibit the translation thereof, but also binding to double-stranded DNA to form a triple strand (triplex) to inhibit the transcription into mRNA.

In the present specification, "complementary" means complementarity of not less than about 70% between base sequences, preferably not less than about 80%, more preferably not less than about 90%, further preferably not less than about 95%, most preferably 100%. The homology of the base sequences in the present specification can be calculated using homology calculation algorithm NCBI BLAST (National Center for Biotechnology Information Basic Local Alignment Search Tool) and under the following conditions (expectancy=10; accept gap; filtering=ON; match score=1; mismatch score=−3).

The aforementioned "ribozyme" refers to an RNA possessing an enzyme activity to cleave a nucleic acid; however, since it has recently been shown that oligo-DNAs having the base sequence of the enzyme activity site also possess nucleic acid cleavage activity, this term is used herein as a concept encompassing DNA, as far as sequence-specific nucleic acid cleavage activity is possessed. Specifically, ribozyme is capable of specifically cleaving the mRNA or initial transcription product that encodes PHD2 in the coding region (in the case of the initial transcription product, the intron portion is included). The most versatile ribozymes are self-splicing RNAs found in infectious RNAs such as viroid and virusoid, and the hammerhead type, the hairpin type and the like are known. The hammerhead type exhibits enzyme activity with about 40 bases in length, and it is possible to specifically cleave the target mRNA alone by making several bases at both ends adjoining to the hammerhead structure portion (about 10 bases in total) to be a sequence complementary to the desired cleavage site of the mRNA. Furthermore, when the ribozyme is used in the form of an expression vector containing the DNA that encodes it, the ribozyme may be a hybrid ribozyme prepared by further joining a sequence modified from the tRNA to promote the migration of the transcription product to cytoplasm [Nucleic Acids Res., 29(13): 2780-2788 (2001)].

The polyanionic substance that suppresses the expression of PHD2 in the present invention can also be provided as an expression vector. Such expression vector includes polynucleotide encoding a PHD2 expression suppressive substance and a promoter operably connected to the polynucleotide.

The aforementioned promoter can be appropriately selected according to the kind of the nucleic acid to be the expression target and under the control thereof. Examples thereof include polIII promoters (e.g., tRNA promoter, U6 promoter, H1 promoter) and promoters for mammal (e.g., CMV promoter, CAG promoter, SV40 promoter).

The expression vector in the present invention may further contain a selection marker gene (gene imparting resistance to medicaments such as tetracycline, ampicillin, kanamycin, hygromycin, phosphinothricine and the like, a gene complementing auxotrophic mutation etc.).

While the backbone of the expression vector in the present invention is not particularly limited as long as it can produce a PHD2 expression suppressing substance in mammalian (e.g., human and the like) cells, for example, plasmid vector and virus vector can be mentioned. Examples of the virus vector include vectors of retrovirus, adenovirus, adeno-associated virus, herpes virus, vaccinia virus, poxvirus, polio virus, sindbis virus, Hemagglutinating Virus of Japan and the like. Among these, a plasmid vector is preferably used for administration to a mammal from the aspect of safety. A vector which expresses siRNA is commercially available, and a commercially available product can also be preferably utilized.

2. Polycation Chargeable Polymer

The polycation chargeable polymer to be used in the present invention is a polymer having a segment chain derived from a chargeable polymer, or a salt thereof. In addition, the polycation chargeable polymer may also be a chargeable homopolymer.

Moreover, the polycation chargeable polymer to be used in the present invention may also be a block copolymer having a segment chain derived from a chargeable polymer and a segment chain derived from a non-ionic hydrophilic polymer, or a salt thereof.

The polycation chargeable polymer in the present invention can be a polymer having a main chain containing polypeptide, polysaccharide, polyester, polyether, polyurethane or vinyl polymer as a base and, as a side chain, a segment chain derived from a chargeable polymer containing a group represented by the formula —NH—(CH$_2$)$_a$—(NH(CH$_2$)$_2$)$_e$—NH$_2$ (wherein a and e are each independently an integer of 1-5), which is bonded to the main chain directly or via a linking group.

Here, the "main chain containing polypeptide as a base" means that a polypeptide formed via a peptide bond between natural or synthetic amino acids is preferably contained as a main chain of the polymer. The natural or synthetic amino acids are preferably amino acids having a cationic group on the side chain, so that the chargeable polymer can be cationic. The cationic group is not limited to a group which has already become cationic by coordination of hydrogen ion, and also includes a group that becomes cationic once hydrogen ion is coordinated. A polypeptide having a cationic group on the side chain also includes, besides those formed by peptide bond of known amino acids having a basic side chain (lysine, arginine, histidine etc.), one having a peptide bond of various amino acids, and a side chain thereof substituted to have a cationic group.

In addition, the "main chain having polysaccharide as a base" means that, for example, a sugar linkage such as DEAE-dextran, chitosan, polygalactosamine or the like is contained as the main chain of a polymer. The "main chain having vinyl polymer as a base" means that a polymer chain formed by polymerization of unsaturated ethyleny polymerizable monomers is contained as the main chain of the polymer.

The side chain to be contained in a polycation chargeable polymer contains a group represented by the formula —NH—$(CH_2)_a$—$(NH(CH_2)_2)_e$—$NH_2$ (wherein a and e are each independently an integer of 1-5), and can be bonded to the aforementioned main chain directly or via a linking group.

When the main chain contains polypeptide as a base, such side chain can be bonded to the main chain, for example, via a carboxyl group present at the β- or γ-position of amino acid, an amino group at the ε-position and the like. When the main chain contains polysaccharide as a base, for example, the side chain can be bonded to the main chain via a hydroxy group, an amino group or a carboxyl group of the saccharide moiety. When the main chain contains a vinyl polymer as a base, for example, the side chain can be bonded to the main chain via a hydroxy group such as poly(vinylalcohol), poly(methacrylamide), poly(acrylamide), poly(methacrylic acid) and the like, an amide group or a carboxyl group.

As a bonding reaction of a main chain and a side chain, a halogen substitution reaction, a condensation reaction utilizing a carboxyl group or an amino group, a transesterification reaction for ester, aminolysis or the like can be used. In addition, a side chain and a main chain may be bonded, for example, via a linking group containing a $C_{1-22}$ alkylene chain. In the present specification, the "$C_{1-22}$ alkylene chain" means a straight chain or branched alkylene group having a carbon number of 1-22. In addition, the linking group may be discontinued by, for example, 1-10 oxygen or sulfur atoms. When a side chain and a main chain are bonded via the linking group, the side chain is generally introduced into a polymer by a polymer reaction, though with no particular limitation thereto.

The molecular weight of the thus-produced polycation chargeable polymer is not particularly limited as long as it can achieve the object of the present invention. The lower limit thereof is generally not less than 1,000, preferably not less than 15,000, more preferably not less than 18,000, and may be set to, for example, not less than 23,000 or not less than 28,000.

In a more specific embodiment of the present invention, the polycation chargeable polymer is a polymer represented by the following formula (III) or a salt thereof.

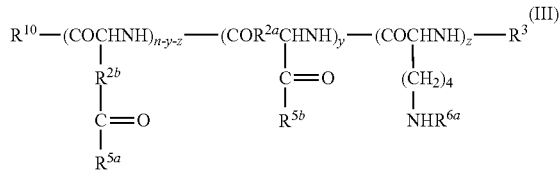

In the above formula, $R^{10}$ is a hydroxy group, an oxybenzyl group or an NH—$R^{11}$ group, and $R^{11}$ is an optionally substituted straight chain or branched $C_{1-20}$ alkyl group. In the present invention, $R^{11}$ is preferably an unsubstituted straight chain or branched $C_{1-20}$ alkyl group. In the present invention, moreover, the $C_{1-20}$ alkyl group for $R^{11}$ may be substituted by one or more substituents. For example, the $C_{1-20}$ alkyl group may be substituted by a substituent selected from the group consisting of an acetalized formyl group, a cyano group, a formyl group, a carboxyl group, an amino group, a $C_{1-6}$ alkoxycarbonyl group, a $C_{2-7}$ acylamide group, a siloxy group, a silylamino group and a tri-$C_{1-6}$ alkyl siloxy group (each alkyl group may be the same or different).

In the present specification, the "$C_{1-20}$ alkyl group" means a straight chain or branched alkyl group having a carbon number of 1-20. Examples of the $C_{1-20}$ alkyl group include methyl, ethyl, n-propyl, isopropyl, n-butyl, sec-butyl, tert-butyl, n-pentyl, n-hexyl, decyl, undecyl, dodecyl, octadecyl, icosyl and the like.

In the present specification, the "$C_{1-6}$ alkoxy group" means a group to which an oxygen atom is bonded to the terminal of a straight chain or branched $C_{1-6}$ alkyl group and, for example, a methoxy group, an ethoxy group, an n-propoxy group, an isopropoxy group, an n-butoxy group, a sec-butoxy group, a tert-butoxy group, an n-pentyloxy group, an n-hexyloxy group and the like can be mentioned.

In the present specification, the "$C_{1-6}$ alkoxycarbonyl group" means a carbonyl group to which the above-mentioned "$C_{1-6}$ alkoxy group" is bonded and, for example, a methoxycarbonyl group, an ethoxycarbonyl group, a 1-propoxycarbonyl group, a 2-propoxycarbonyl group, a 2-methyl-2-propoxycarbonyl group and the like can be mentioned.

In the present specification, the "$C_{2-7}$ acyl group" means a carbonyl group to which a straight chain or branched $C_{1-6}$ alkyl group is bonded and, for example, an acetyl group, a propionyl group, an isopropionyl group, a butyryl group, an isobutyryl group and the like can be mentioned.

In the present specification, the "$C_{2-7}$ acylamide group" means an amino group to which the above-mentioned "$C_{2-7}$ acyl group" is bonded. The groups other than $R^{10}$, which are included in the above-mentioned formula (III), are described later.

While respective repeat units in the above-mentioned formula (III) are shown in a particular order for the convenience of description, each repeat unit can be present at random. For example, a chargeable polymer may be a main chain having, as a base, a polypeptide in which each repeat unit in the above-mentioned formula (III) starts from the N terminal.

In addition, a polymer represented by the above-mentioned formula (III) may also be, as one embodiment of the present invention, a salt of a polymer represented by the above-mentioned formula (III). While the salt is not particularly limited, a salt with, as a counter ion, $Cl^-$, $Br^-$, $I^-$, $(1/2SO_4)^-$, $NO_3^-$, $(1/2CO_3)^-$, $(1/3PO_4)^-$, $CH_3COO^-$, $CF_3COO^-$, $CH_3SO_3^-$, $CF_3SO_3^-$ or the like can be mentioned.

The non-ionic hydrophilic polymer in the present invention is not particularly limited as long as it is a polymer which is non-ionic and hydrophilic. Examples of the non-ionic hydrophilic polymer include poly(ethylene glycol), poly(vinylalcohol), poly(vinylpyrrolidone), poly(methacrylamide), poly(acrylamide), poly(hydroxyethylmethacrylate) and poly(hydroxyethylacrylate). A preferable non-ionic hydrophilic polymer among these is polyethylene glycol.

The non-ionic hydrophilic polymer can be produced by using, for example, the method described in WO96/32434, WO96/33233 or WO97/06202.

In another embodiment of the present invention, the polycation chargeable polymer used in the present invention may be a block copolymer having a segment chain derived from the above-mentioned chargeable polymer and a segment chain derived from a non-ionic hydrophilic polymer, or a salt thereof. In addition, specific examples of such block copolymer include a block copolymer represented by the formula (I) or (II), or a salt thereof.

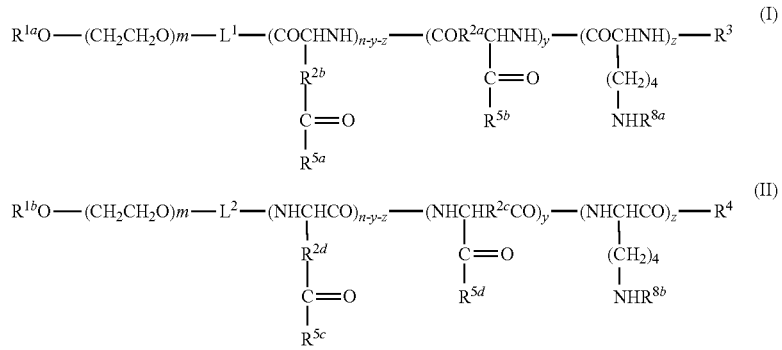

In the above-mentioned formula (I) or (II), $R^{1a}$ and $R^{1b}$ are each independently a hydrogen atom or an optionally substituted straight chain or branched $C_{1-12}$ alkyl group. In the present specification, the "$C_{1-12}$ alkyl group" means a straight chain or branched alkyl group having a carbon number of 1-12. Examples of the $C_{1-12}$ alkyl group include methyl, ethyl, n-propyl, isopropyl, n-butyl, sec-butyl, tert-butyl, n-pentyl, n-hexyl, decyl, undecyl, dodecyl and the like.

In addition, the alkyl group in the present invention may be substituted by one or more substituents. Examples of the substituent when it is substituted include an acetalized formyl group, a cyano group, a formyl group, a carboxyl group, an amino group, a $C_{1-6}$ alkyl siloxy group, a $C_{2-7}$ acylamide group, a siloxy group, a silylamino group, a tri-$C_{1-6}$ alkyl siloxy group (each alkyl group may be the same or different) and the like. Acetalization is one of the methods for protecting carbonyl of a formyl group, and means that an acetal moiety is formed by a reaction of carbonyl of a formyl group and, for example, 2 alkanols having a carbon number of 1-6 or optionally branched alkylenediol having a carbon number of 2-6. In addition, substituents can be converted to other groups under appropriate conditions. For example, when the substituent is an acetalized formyl group, it can be converted to other substituent, a formyl group (aldehyde group etc.), by hydrolysis under mild acidic conditions. In addition, when the substituent is a formyl group, a carboxyl group or an amino group, the substituent can be utilized, for example, for imparting functionality or target directivity to a carrier by binding the substituent to an antibody, a fragment having specific affinity thereof ($F(ab')_2$, F(ab) etc.) or the like. In the present invention, $R^{1a}$ and $R^{1b}$ are preferably methyl groups.

In the above-mentioned formula (I) or (II), $R^{2a}$, $R^{2b}$, $R^{2c}$ and $R^{2d}$ are each independently a methylene group or an ethylene group, preferably a methylene group. When both $R^{2a}$ and $R^{2b}$ are methylene groups, the main chain of the repeat unit corresponds to poly(aspartic acid derivative), and when they are ethylene groups, it corresponds to poly (glutamic acid derivative). In these formulas, when $R^{2a}$ and $R^{2b}$, or $R^{2b}$ and $R^{2a}$, are a methylene group and an ethylene group, respectively, and when $R^{2c}$ and $R^{2d}$, or $R^{2d}$ and $R^{2c}$, are a methylene group and an ethylene group, respectively, the repeat units of the aspartic acid derivative and glutamic acid derivative can be present to form respective blocks, or can be present at random.

$R^3$ in the above-mentioned formula (I) is a hydrogen atom, a protecting group, a hydrophobic group or a polymerizable group. Here, the "protecting group" is not particularly limited as long as it is generally used as an amino-protecting group. Examples of the protecting group include a Z group (benzyloxycarbonyl group), a Boc group (tert-butoxycarbonyl group), an acetyl group, a trifluoroacetyl group and the like. In addition, while the hydrophobic group is not particularly limited, it is, for example, an alkyl group, a cycloalkyl group or an aryl group. In addition, a polymerizable group may be any functional group that causes a polymerization reaction, and examples thereof include, but are not particularly limited to, an unsaturated hydrocarbon group. More specifically, the polymerizable group is a vinyl group, an allyl group, an acrylic group, an acryloyl group, a methacryloyl group, a propenyl group, a vinylidene group, a vinylene group, an isocyanate group, an isothiocyanate group, a carboxyl group, a hydroxy group, an amino group, an alkoxy group and the like. Of these, $R^3$ is preferably an acetyl group, an acryloyl group or a methacryloyl group. In another embodiment of the present invention, $R^3$ is preferably a hydrogen atom.

$R^4$ in the above-mentioned formula (II) is a hydroxy group, a protecting group, a group represented by —O—$X^3$, —S—$X^3$ or —NH—$X^3$, or a polymerization initiator residue of polypeptide. Here, the protecting group may be any group that is used as a protecting group of a terminal carboxyl group and, examples thereof include, but are not particularly limited to, a group that forms, together with a carboxyl group, alkyl ester (e.g., methyl ester, ethyl ester, tert-butyl ester etc.) or benzyl ester. In addition, while $X^3$ is not particularly limited, it is preferably a compound residue that does not interfere with a series of reactions of a desired polymer synthesis. Examples of $X^3$ include a primary, secondary or tertiary amine compound, an amine compound residue containing one or more groups derived from a quaternary ammonium salt, and a non-amine compound residue. Moreover, the "initiator" means a substance used for starting the polymerization reaction of polypeptide and, for example, butylamine can be mentioned. Furthermore, the "initiator residue" means a residue derived from an initiator contained in the polymer as a result of the polymerization reaction. In the present invention, $R^4$ is preferably —NH—$R^9$, and $R^9$ is an optionally substituted straight chain or branched $C_{1-20}$ alkyl group.

$R^{5a}$, $R^{5b}$, $R^{5c}$ and $R^{5d}$ in the above-mentioned formula (I) or (II) are each independently a hydroxy group, an oxybenzyl group or an NH—$(CH_2)_a$—X group. Here, a is an integer of 1-5, each X is independently a primary, secondary or tertiary amine compound, an amine compound residue containing one or more groups derived from a quaternary ammonium salt, or a non-amine compound residue. Furthermore, in the above-mentioned formulas (I)-(III), two or more of the total of $R^{5a}$ and $R^{5b}$, or the total of $R^{5c}$ and $R^{5d}$ are an —NH—$(CH_2)_a$—$X^1$ group (wherein $X^1$ is $(NH(CH_2)_2)_e$—$NH_2$, and e is an integer of 1-5). The total means the number of "$R^{5a}$ and $R^{5b}$" or "$R^{5c}$ and $R^{5d}$" contained in a block copolymer represented by the above-mentioned formula (I) or (II), or a polycation chargeable polymer represented by the above-mentioned formula (III).

In another embodiment of the present invention, a block copolymer comprising not less than 50%, further not less than 85%, of the total of $R^{5a}$ and $R^{5b}$, or $R^{5c}$ and $R^{5d}$, wherein these groups are each an —NH—$(CH_2)_a$—$X^1$ group (wherein $X^1$ is $(NH(CH_2)_2)_e$—$NH_2$, and e is an integer of 1-5), is preferably used.

Moreover, in another embodiment of the present invention, all of $R^{5a}$ and $R^{5b}$, or all of $R^{5c}$ and $R^{5d}$, contained in a polycation chargeable polymer represented by the above-mentioned formulas (I)-(III), are preferably —NH—$(CH_2)_a$—$X^1$ groups (wherein $X^1$ is $(NH(CH_2)_2)_e$—$NH_2$, a is 2 or 3, and e is an integer of 1-3, particularly preferably e is 1).

Furthermore, in the present invention, $R^{5a}$, $R^{5b}$, $R^{5c}$ and $R^{5d}$ are particularly preferably —NH—$NH_2$ or —NH—$(CH_2)_2$—NH—$(CH_2)_2$—$NH_2$. Of these, —NH—$(CH_2)_2$—NH—$(CH_2)_2$—$NH_2$ containing a diethylenetriamine unit is most preferable.

In addition, in the present invention, X may be any group selected from the group consisting of —$NH_2$, —NH—$CH_3$, —$N(CH_3)_2$ and groups represented by the following formulas.

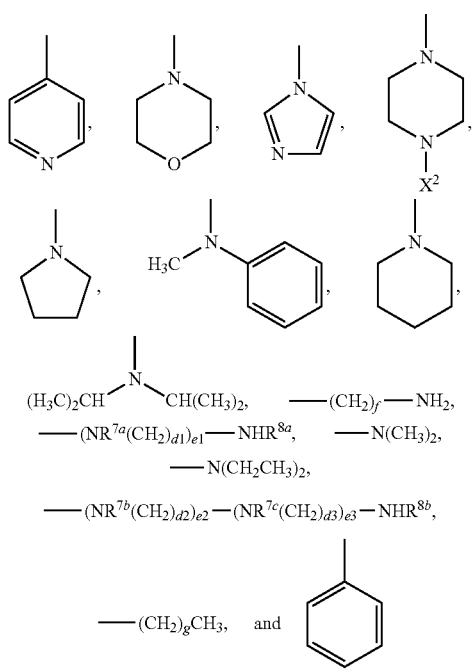

In each of the above-mentioned formulas, $X^2$ is a hydrogen atom, a $C_{1-6}$ alkyl group or an amino $C_{1-6}$ alkyl group, $R^{7a}$, $R^{7b}$ and $R^{7c}$ are each independently a hydrogen atom or a methyl group, d1, d2 and d3 are each independently an integer of 1-5, e1, e2 and e3 are each independently an integer of 1-5, f is an integer of 0-15, and $R^{8a}$ and $R^{8b}$ are each independently a hydrogen atom or a protecting group. Here, the protecting group is selected from the group consisting of a Z group, a Boc group, an acetyl group and a trifluoroacetyl group, and g is an integer of 0-15.

$R^{6a}$ and $R^{6b}$ in the above-mentioned formulas (I)-(III) are each independently a hydrogen atom or a protecting group. Here, the protecting group is selected from the group consisting of a Z group, a Boc group, an acetyl group and a trifluoroacetyl group, which are generally used as amino-protecting groups.

$L^1$ and $L^2$ in the above-mentioned formulas (I) and (II) are linking groups.

$L^1$ to be a linker moiety in the above-mentioned formula (I) is preferably —S—S—, —NH— or a group represented by the formula: —$(CH_2)_b$—NH— (wherein b is an integer of 1-5), and $L^2$ to be a linker moiety in the above-mentioned formula (II) is preferably —S—S—, —CO— or a group represented by the formula: —$(CH_2)_c$—CO— (wherein c is an integer of 1-5). In addition, $L^1$ and $L^2$ may further have OCO, OCONH, NHCO, NHCOO, NHCONH, CONH, COO or the like.

m, n, y and z in the above-mentioned formulas (I)-(III) show the numbers of repeat units of each block moiety (degree of polymerization). To be specific, m is an integer of 5-20,000, n is an integer of 2-5,000, y is an integer of 0-5,000, and z is an integer of 0-5,000, and n is not bigger than y+z. Preferably, z is 0. In the present invention, when, for example, z is 0 (zero), a polycation chargeable polymer wherein $R^3$ is an acetyl group, an acryloyl group or a methacryloyl group can be mentioned. In the above-mentioned formulas (I)-(III), respective repeat units are shown in a particular order for the convenience of description. Each repeat unit can be present at random.

A polymer represented by the above-mentioned formula (I) or (II) may be a salt of the polymer represented by the above-mentioned formula (I) or (II). While the salt is not particularly limited, a salt with, as a counter ion, $Cl^-$, $Br^-$, $I^-$, $(1/2\ SO_4)^-$, $NO_3^-$, $(1/2\ CO_3)^-$, $(1/3\ PO_4)^-$, $CH_3COO^-$, $CF_3COO^-$, $CH_3SO_3^-$, $CF_3SO_3^-$ or the like can be mentioned.

The method of producing the block copolymer in the present invention is not limited; examples include a method wherein a segment chain derived from a nonionic hydrophilic polymer is synthesized in advance, and specified monomers are sequentially polymerized to one end (the end opposite to $R^{1a}$ or $R^{1b}$) of this segment chain derived from a nonionic hydrophilic polymer, after which the side chain is substituted or converted so that the side chain will contain a cationic group as required, or a method wherein a segment chain derived from a nonionic hydrophilic polymer and a segment chain derived is from a chargeable polymer are synthesized in advance, and these are joined together, and the like. The methods and conditions for the various reactions in the respective manufacturing process can be chosen or set as appropriate in consideration of conventional methods. For example, an example method of production is described in JP-A-2004-352972, and the block copolymer can be produced according to methods described therein or methods modified therefrom.

While the average molecular weight (Mw) of the thus-produced block copolymer is not particularly limited, it is preferably 23,000-45,000, more preferably 28,000-34,000. In each block moiety, the average molecular weight (Mw) of a segment chain derived from a non-ionic hydrophilic polymer is preferably 8,000-15,000, more preferably 10,000-12,000, and the average molecular weight (Mw) of a segment chain derived from a chargeable polymer is preferably 15,000-30,000, more preferably 18,000-22,000.

In the present invention, glycosaminoglycan can also be further used. The glycosaminoglycan is also called mucopolysaccharide, meaning a series of acidic polysaccharides including amino sugar, which are biocompatible polymers universally present in living organisms. Hence, glycosaminoglycan is a biocompatible polymer almost non-toxic and innocuous for living organisms.

In the present invention, as glycosaminoglycan, any of those extracted from naturally occurring substances such as animal and the like, those extracted from cultures of microorganisms, those chemically or enzymatically synthesized and the like can be used. In addition, in the present invention, a commercially available product of glycosaminoglycan can also be used.

In the present invention, when glycosaminoglycan is used to form a polyion complex together with a polyanionic substance that suppresses PHD2 expression and a polycation chargeable polymer, the complex is further stabilized, and can prevent easy damage to the tissues. The thus-formed polyion complex is also referred to as a ternary system complex. Examples of glycosaminoglycan to be used in the present invention include chondroitin sulfate A, chondroitin sulfate B, chondroitin sulfate C, chondroitin, hyaluronic acid, heparin, keratansulfuric acid, heparansulfuric acid, chitosan and salts thereof. Of these, chondroitin sulfate and a salt thereof are preferable since they are present in a high amount in the extracellular matrix, and are one of the main constituent components of the body. Of these, chondroitin sulfate A and a salt thereof are more preferable.

3. Pharmaceutical Composition

The polyion complex to be used for the pharmaceutical composition of the present invention can be easily prepared by mixing a polyanionic substance that suppresses PHD2 expression and a polycation chargeable polymer, and glycosaminoglycan as necessary, in any buffer (e.g., aqueous medium, preferably, medium containing deionized water as a base), and generally standing or stirring the mixture at 4-25° C. for 0.5-24 hr. Where necessary, operations such as dialysis, stirring, dilution, concentration, sonication, temperature control, pH control, ion strength control, addition of organic solvent and the like can be added as appropriate.

A method of mixing a PHD2 expression suppressing substance, a polycation chargeable polymer and glycosaminoglycan is not particularly limited and, for example, one kind each may be mixed or all three kinds may be mixed at once. The mixing may be performed by adding a small amount by, for example, dropwise addition to contact each component, or increasing an amount of contact with time, or contacting the total amount of the components at once. In addition, the order of mixing each component is not particularly limited, and glycosaminoglycan may be mixed with a polycation chargeable polymer in advance and a PHD2 expression suppressing substance may be mixed with the obtained mixture; or a PHD2 expression suppressing substance may be mixed with a polycation chargeable polymer in advance and glycosaminoglycan may be further mixed with the mixture; or glycosaminoglycan and a PHD2 expression suppressing substance may be mixed and then a polycation chargeable polymer may be mixed therewith.

Because a PHD2 expression suppressing substance is polyanionic, a polyion complex in the present invention refers to a state wherein when this is mixed with a polycation chargeable polymer, an electrostatic bond is formed by the two. Hence, when a PHD2 expression suppressing substance and a polycation chargeable polymer are mixed together, an electrostatically bound polyion complex can be formed due to the negative charge of the suppressant and the positive charge of the chargeable polymer. When the polycation chargeable polymer has a segment chain derived from a nonionic hydrophilic polymer, a non-macromolecular micelle in what is called a core-shell type form wherein the segment chain constitutes the shell moiety and the segment chain derived from a chargeable polymer and a PHD2 expression suppressing substance constitute the core moiety can be constructed.

When the pharmaceutical composition of the present invention further comprises glycosaminoglycan, an electrostatic interaction arises from the negative charge possessed by the PHD2 expression suppressing substance and the positive charge possessed by the polycation chargeable polymer, based on which a ternary system complex is formed. In this case, any of a negatively charged glycosaminoglycan such as chondroitin sulfate, hyarulonic acid or heparan sulfate and a positively charged glycosaminoglycan like chitosan and the like can be used according to the concentrations of the PHD2 expression suppressing substance and polycation chargeable polymer. Provided that a polyion complex consisting of a PHD2 expression suppressing substance and polycation chargeable polymer is formed in advance, and this is followed by adding glycosaminoglycan, it is possible to configure a ternary system complex such that the glycosaminoglycan covers the surface of the polyion complex, hence to further stabilize the PHD2 expression suppressing substance and to ameliorate the cytotoxicity derived from a polycation chargeable polymer.

A polyion complex in the present invention can be prepared by mixing solutions of a PHD2 expression suppressing substance and of a polycation chargeable polymer, and, as required, of glycosaminoglycan, in an appropriate blending ratio. For example, when a nucleic acid is used as the PHD2 expression suppressing substance, the blending ratio of the nucleic acid and polycation chargeable polymer can be expressed as the ratio, of the total number of cations in the polycation chargeable polymer (N) and the total number of phosphoric acid ester bonds or equivalent bonds contained in the nucleic acid (P) (N/P ratio). Here, being equivalent to the phosphoric acid ester bond refers to a bond formed between nucleosides in a portion of the nucleic acid for the purpose of achieving stability in living organisms, such as higher nuclease resistance than by the phosphoric acid ester bond and the like, and is exemplified by phosphorothioate, phosphorodithioate, phosphoroamidate, boranophosphate, phosphoroselenate, or methylphosphoroate and the like. When the equivalent bond has a charge equivalent to that of phosphoric acid ester bond (−1), P can be obtained by summing the two; when the equivalent bond has no charge (O), or when the equivalent bond has a positive charge (+1), or when the equivalent bond has two negative charges (−2), P can be calculated by subtracting each charge from the total number of phosphoric acid ester bonds (−1). The total number of cations in the polycation chargeable polymer (N) is the total number of cationic amino groups in any one of the foregoing formulas (I)-(III).

In the present invention, the aforementioned N/P ratio is not limited as long as a polyion complex can be formed, and varies depending on the properties of the non-charged segment or charged segment contained in the polycation chargeable polymer. Hence, the N/P ratio in the present invention can be appropriately determined by those of ordinary skill in the art.

While the N/P ratio in the present invention is not particularly limited, for example, the ratio can be set to 0.5-160, preferably 1-120, more preferably 2-80, further preferably 10-80. Particularly, when the polycation chargeable polymer is a block copolymer of the above-mentioned formula (I) or (II), while the N/P ratio is not particularly limited, it can be preferably set to 1-120, more preferably 2-80, further more preferably 10-80.

When glycosaminoglycan is used as the polyion complex in the present invention, the concentration thereof after mixing can be set to 0.001-100 mg/ml, preferably 0.01-50 mg/ml, more preferably 0.05-5 mg/ml.

In addition, the aforementioned glycosaminoglycan can be added at 1/50-1/2 volume, preferably 1/20-1/5 volume, more preferably 1/10 volume, relative to the content of a polycation chargeable polymer or a complex of a polycation chargeable polymer and a PHD2 expression suppressing substance, or the amount of a solution containing them.

The average particle diameter of the polyion complex in the present invention is normally 30-200 nm, preferably 30-150 nm, more preferably 50-100 nm. The particle size distribution index is normally 0.1-0.3. Methods of measuring the average particle diameter and particle size distribution index include, for example, a method using a dynamic light scattering photometer (for example, DLS-7000DH model, manufactured by Otsuka Electronics Co., Ltd). A polyion complex having an average particle diameter of about 50-200 nm is favorable in that it can be recovered at extremely high 2.5 yields to enable efficient supply of injections, even when subjected to eradicating filtration using a 0.22 μm filter for use in preparing injections (for subcutaneous injection, for venous injection, for arterial injection, for intramuscular injection, for intraperitoneal injection and the like).

The pharmaceutical composition of the present invention may further comprise a pharmaceutically acceptable carrier, and can be administered non-orally as an intravenous, intra-arterial, intramuscular, intraperitoneal or subcutaneous injection. In this case, the composition is provided in the form of a unit dosage ampoule or multiple dosage container. The composition can also be prepared as a freeze-dried product as required by a method known per se. As the pharmaceutically acceptable carrier, various organic or inorganic carrier substances in common use as pharmaceutical materials can be used, which are formulated as solvents, solubilizers, suspending agents, isotonizing agents, buffering agents, soothing agents and the like. Pharmaceutical additives such as antiseptics, antioxidants, and coloring agents can also be used as necessary. Examples of suitable solvents include water for injection, alcohols, propylene glycol, macrogol, sesame oil, corn oil and the like. Examples of suitable stabilizers include polyethylene glycol, propylene glycol, D-mannitol, benzyl benzoate, ethanol, trisaminomethane, cholesterol, triethanolamine, sodium carbonate, sodium citrate and the like. Examples of suitable suspending agents include surfactants such as stearyltriethanolamine, sodium lauryl sulfate, laurylaminopropionic acid, lecithin, benzalkonium chloride, benzethonium chloride, and glyceryl monostearate; hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose; and the like. Examples of suitable isotonizing agents include buffer solutions such as of phosphates, acetates, carbonates, and citrates, and the like. Examples of suitable soothing agents include benzyl alcohol and the like. Examples of suitable preservatives include paraoxybenzoic acid esters, chlorobutanol, benzyl alcohol, phenethyl alcohol, dehydroacetic acid, sorbic acid and the like. Examples of suitable antioxidants include sulfites, ascorbic acid and the like.

Dosage forms of the pharmaceutical composition of the present invention include injections; the composition can be administered intravenously, intra-arterially, intraperitoneally, intramuscularly, intra-articularly, subcutaneously, intradermally and the like; any method of administration can be used according to the site for delivery. In intravenous administration, drip infusion, bolus injection and the like are possible; when a skeletal muscle is the target, intramuscular injection or topical intravenous administration using a tourniquet can be utilized. Furtheimore, a dosage form using a catheter can also be employed. In this case, the composition is normally provided in the form of a unit dosage ampoule or multiple dosage container. For example, in the case of administration into the heart, a catheter may be inserted from the femoral artery at the base of one leg or the brachial artery in one elbow to reach the coronary artery of the heart, where the pharmaceutical composition of the present invention can be intracoronarily administered. Administration can be achieved using not only an ordinary catheter, but also a catheter of low invasion. When various materials such as balloons and stents are used, the pharmaceutical composition of the present invention may be applied to the surface of the material to obtain a form such as a medical device with the capability of sustained release to the destination site. In the case of administration to a lower limb, the pharmaceutical composition of the present invention may be administered while compressing the lower limb with elastic stocking used in combination, or may be administered to a deep vein after high ligation of the saphenous vein.

The amount of the pharmaceutical composition of the present invention administered varies depending on the purpose of treatment, the recipient's age, route for administration, and frequency of administration, and can be changed over a wide range; the amount of PHD2 expression suppressing substance contained in the pharmaceutical composition of the present invention can be set as appropriate by those skilled in the art, and is, for example, 0.01 μg-10,000 μg per kg body weight per dose; doses are given at intervals of 3 days to 4 weeks.

The pharmaceutical composition of the present invention is superior in the stability in the body and retentivity in blood, and low toxic. The pharmaceutical composition of the present invention is useful as an agent for the treatment or prophylaxis of diseases in a mammal (e.g., human, mouse, rat, hamster, guinea pig, rabbit, swine, bovine, goat, horse, sheep, canine, feline, monkey, orangutan, chimpanzee etc.).

Although the disease targeted by the pharmaceutical composition of the present invention is not particularly limited, as far as treatment by the PHD2 expression suppressing action is intended, ischemic diseases or arterial diseases are preferable because the angiogenesis effect exhibited by the pharmaceutical composition of the present invention is excellent. Ischemic diseases or arterial diseases include ischemic cardiac diseases, myocardial infarction, cardiomyopathy, angina pectoris, unstable angina pectoris, coronary sclerosis, cardiac failure, arteriosclerosis obliterans, Buerger's disease, vascular injury, artery obstruction, arterial thrombosis, organ artery obstruction, aneurysms, ischemic brain diseases, ischemic lung diseases, renal infarction and the like.

In another aspect, the present invention provides a therapeutic or prophylactic method for ischemic disease or arterial disease comprising a step for administering the above-described pharmaceutical composition to a subject in need thereof. Specific examples of ischemic diseases or arterial diseases are the same as those shown above. The method of administration, form of administration and recipient of administration for the pharmaceutical composition are also the same as those shown above.

EXAMPLES

The present invention is explained in more detail in the following by referring to Examples, to which the present invention is not limited.

1. Preparation of RNA Expression Plasmid

As a polyanionic substance that suppresses the expression of PHD2, an expression plasmid of siRNA against mouse PHD2 was constructed. An oligonucleotide having the following base sequence:
5'-GAACTCAAGCCCAATTCAG-3' (siPHD2-A) (SEQ ID NO: 3) or
5'-TGAGCGAGCGAGAGCTAAA-3' (siPHD2-B) (SEQ ID NO: 4) was used as a sense strand of DNA corresponding to mouse PHD2 siRNA. In addition, an oligonucleotide having a base sequence (21 bases) free of homology with mouse gene was used as a sense strand of DNA corresponding to control siRNA. These oligonucleotides were purchased from Hokkaido System Co., Ltd. According to the attached protocol, respective oligonucleotides were conjugated with an expression vector pSilencer2.1-U6 (No. 5762, manufactured by Ambion) incorporating human U6 promoter or an expression vector pSilencer4.1-CMV (No. 5775, manufactured by Ambion) incorporating cytomegalovirus promoter, whereby siRNA(shRNA) expression plasmid against mouse PHD2 and control siRNA(shRNA) expression plasmid were constructed. The following experiment was performed by using siPHD2-A expression vector.

2. Synthesis of Polycation Chargeable Polymer 2-1. Synthesis of poly(N-(2-aminoethyl)-aminoethylaspartamide)

β-Benzyl-L-aspartate-N-carboxylic acid anhydride (BLA-NCA) was dissolved in a mixed solvent of N,N-dimethylformamide (DMF) and dichloromethane, and a polymerization reaction was performed at 40° C. for 2 days using butylamine as an initiator. The N-terminal was acetylated with acetic anhydride, which was followed by reprecipitation with diethylether and drying to give a poly(β-benzyl-L-aspartate) (PBLA) polymer. PBLA was dissolved in DMF, diethylenetriamine in an amount corresponding to 50-fold equivalents of benzyl ester was added, and the mixture was reacted at 40° C. for 1 day. The reaction mixture was added dropwise to aqueous acetic acid solution, placed in a dialysis tube, and dialyzed against 0.01N hydrochloric acid as an external fluid. After evaporation, the residue was freeze-dried to give poly (N-(2-aminoethyl)-aminoethylaspartamide) as a white powder. The obtained polymer (hereinafter sometimes to be referred to as "PAspDET") was hydrochloride of a polymer shown by the following structural formula (n=98).

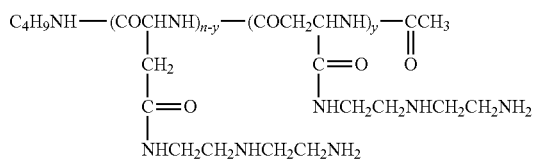

2-2. Synthesis of polyethylene glycol-poly(N-(2-aminoethyl)-aminoethylaspartamide) block copolymer Polyethylene glycol having methoxy on one terminal and aminopropyl on the other terminal, and an average molecular weight of 12,000 (hereinafter sometimes to be referred to as "PEG") was dissolved in dichloromethane, and BLA-NCA was dissolved in a mixed solvent of DMF and dichloromethane and the mixture was reacted at 40° C. for 2 days. The N terminal was acetylated with acetic anhydride to give polyethylene glycol-block-poly(β-benzyl-L-aspartate) (PEG-PBLA). By NMR analysis, the degree of polymerization of the PBLA moiety was 68. In the following, a block copolymer with a molecular weight of PEG of 12,000, and the degree of polymerization of PBLA moiety of 68 may be indicated as PEG-PBLA(12-68) (the number 12 in the parenthesis shows a molecular weight of 12,000, and 68 shows the degree of polymerization).

The thus-obtained PEG-PBLA(12-68) was dissolved in benzene and freeze-dried, and then dissolved in DMF under an argon atmosphere. To this solution was added diethylenetriamine dried by distillation and purified in an amount 50-fold equivalent to benzyl ester, and the mixture was stirred under an argon atmosphere at 40° C. for 24 hr. The reaction solution was added dropwise to 10% acetic acid, dialyzed against 0.1N—HCl by using a dialysis membrane with a fraction molecular weight of 3500. The dialysis membrane internal solution was recovered and lyophilized to give a PEG-PAsp(DET) block copolymer represented by the following structural formula (V) (hereinafter sometimes to be referred to as "PEG-PAsp(DET)") in the form of a hydrochloride in a white solid.

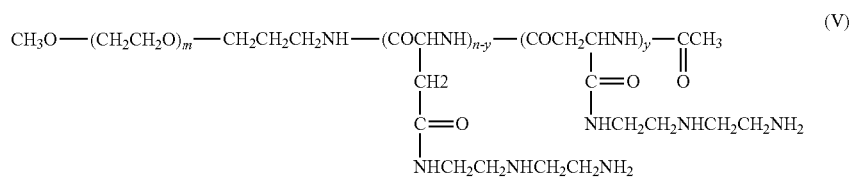

(V)

2-3. Synthesis of polyethylene glycol-polylysine block copolymer

Nε-Z-L-lysin N carboxylic acid anhydride was polymerized using polyethylene glycol of one terminal primary amino group as an initiator. The reaction solution was added dropwise to cold ether and the resulting polyethylene glycol-poly (Nε-Z-L-lysin) block copolymer (PEG-PLL(Z)) was collected by filtration. PEG-PLL(Z) was dissolved in trifluoroacetic acid, deprotected by using HBr acetic acid, and ether reprecipitation, dialysis and freeze-drying were performed to give polyethylene glycol-polylysine block copolymer (hereinafter sometimes to be referred to as "PEG-PLL").

3. Preparation of Polyion Complex

A polyion complex of siRNA expression plasmid against PHD2 prepared as mentioned above (hereinafter sometimes to be referred to as "shPHD2") or control siRNA expression plasmid (hereinafter sometimes to be referred to as "shCont"), and the above-mentioned each polycation chargeable polymer was prepared by mixing each plasmid solution and each polymer solution 30 min to 1 hr before administration. Each polymer solution was prepared by dissolving a polymer produced in a solid in 10 mM Tris-HCl buffer (pH 7.5) to a concentration of 5500 μg/ml (PEG-PAsp(DET)) or 230 μg/ml (PEG-PLL). Each polymer solution and each plasmid solution were mixed at a volume mixing ratio of 2:1, and the concentration of the polymer in the obtained polyion complex is 1/3 of the aforementioned concentration. The polymers used in this Example were PEG-PAsp(DET)(20) and PEG-PLL(2). The numerical value of each polymer in the parenthesis shows N/P ratio. The DNA final concentration was 33.3 μg/ml.

A polyion complex added with chondroitin sulfate (chondroitin sulfate A sodium salt: manufactured by Sigma) was prepared as follows. First, chondroitin sulfate was dissolved in pure water to prepare a chondroitin sulfate solution at a concentration of 50 mg/ml. Next, 1/10 volume of the chondroitin sulfate solution was added to a solution containing a polyion complex of each plasmid and each polymer prepared as mentioned above, and the mixture was stood for 30 min.

4. Experimental Animal

8-Week-old male BALB/c mice were purchased from Oriental Yeast Co., Ltd. All mice were reared with free ingestion of a high-pressure sterilized feed and sterilized water. All animal studies were performed according to the principles of the guideline relating to the animal experiments by the University of Tokyo.

Example 1

Influence of shPHD2 Administration in Ischemia Model Mouse

Using 8-week-old male BALB/c mice, left lower leg ischemia model mouse was prepared by ligating the femoral artery region of origin of the left lower leg. The mice were divided into 4 groups with 5-6 mice per group and, one day after femoral artery ligation, (A) polyion complex of shCont and PEG-PAsp(DET) (hereinafter to be referred to as "shCont+PEG-PAsp(DET)"), (B) shPHD2 alone (hereinafter to be referred to as "naked shPHD2"), (C) polyion complex of shPHD2 and PEG-PLL (hereinafter to be referred to as "shPHD2+PEG-PLL"), and (D) polyion complex of shPHD2, PEG-PAsp(DET) and chondroitin sulfate (hereinafter to be referred to as "shPHD2+PEG-PAsp(DET)") were each injected from the left lower leg great saphenous vein of the mice in each group. The injection volume of shPHD2 and shCont was 50 μg (300 μL as the solution). On day 21, the condition of the lower leg of the mice in each group was examined by visual observation of the appearance, and the representative case was photographed. The representative photographs are shown in FIG. 1, in which an arrow shows the left lower leg of the mice subjected to the ischemia treatment.

As a result, as shown in the photograph of FIG. 1, in shPHD2 administration groups (B)-(D), all mice had no problem in the appearance, and the left lower leg was intact. In contrast, in (A) shCont administered group, the left lower legs of the mice were not preserved but necrotized and disappeared in appearance.

Example 2

Analysis of Blood Flow State in Ischemia Model Mouse

The left lower leg ischemia model mice in 4 groups of (A) shCont+PEG-PAsp(DET), (B) naked shPHD2, (C) shPHD2+ PEG-PLL, and (D) shPHD2+PEG-PAsp(DET), that had been treated as shown in Example 1, were analyzed for the blood flow state by using a laser Doppler blood flow imaging apparatus (moorLDI Laser Doppler Imager, Moor Instruments Ltd., England) and software (MLDI VS.1 S/N 5409, Moor Instruments Ltd., England). As for the blood flow state, the state before treatment, after treatment, day 3, day 7, day 14 and day 21 was analyzed, and the representative case in each group was photographed by the same blood flow imaging apparatus. The representative photographs thereof are shown in FIG. 2.

Figure 2:
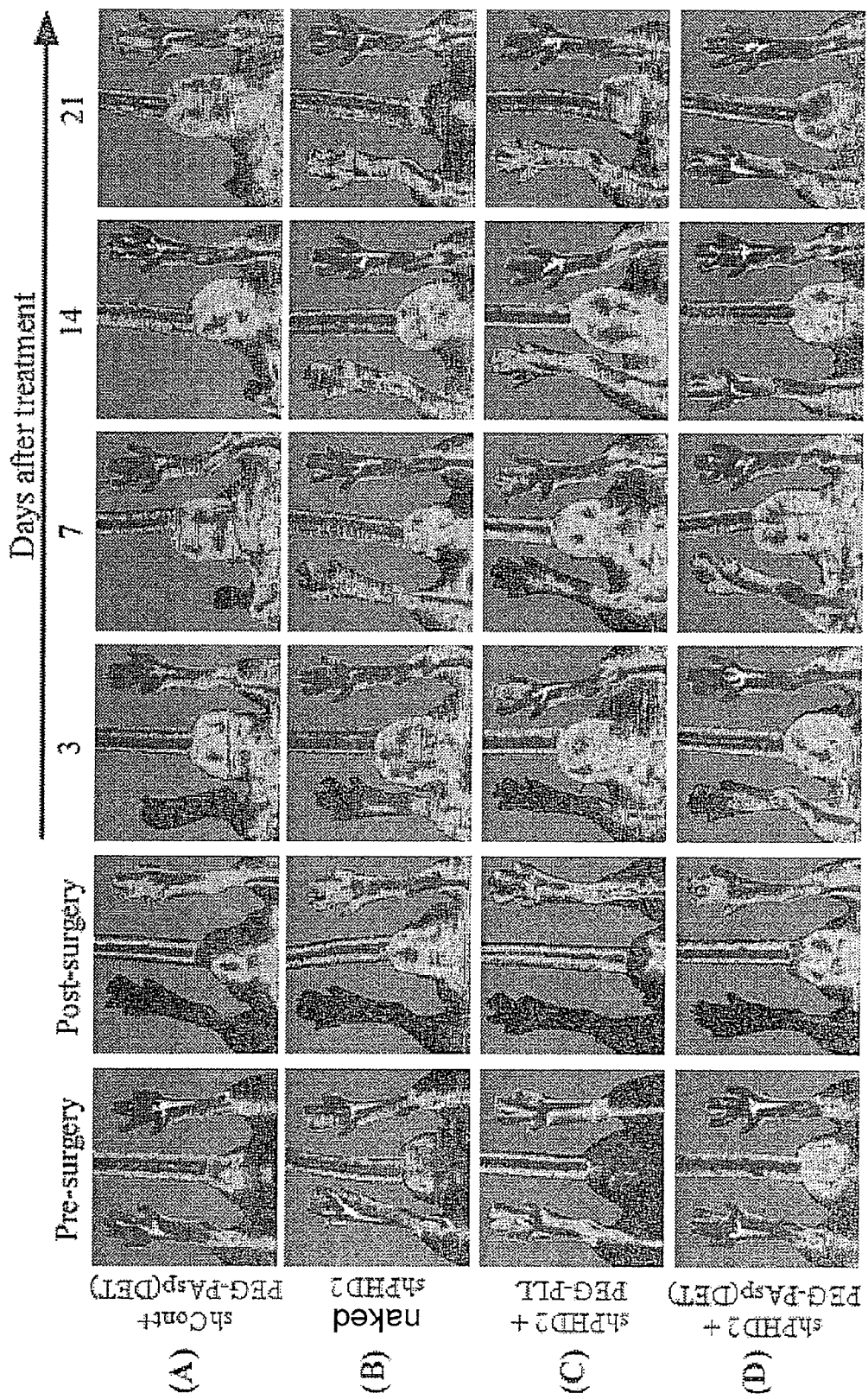
FIG. 2 shows the blood flow of lower legs of mouse administered with various test samples after an ischemia treatment. In (A), shRNA expression plasmid (control) was administered by using PEG-PAsp (DET), in (B), shRNA expression plasmid of PHD2 was administered without using a polycation chargeable polymer, in (C), shRNA expression plasmid of PHD2 was administered by using PEG-PLL and in (D), shRNA expression plasmid of PHD2 was administered by using PEG-PAsp (DET).

As shown in the photographs of FIG. 2, the mice in group (A) showed no blood flow in the left lower leg from after the treatment to day 3, and showed necrosis of the left lower leg followed by disappearance of the leg from day 7 and thereafter. In contrast, the mice in groups (B)-(D) all showed blood flow in the left lower leg on day 21 after the treatment. Particularly, in group (D), the blood started to flow in the left lower leg from day 3 after the treatment and the blood flow was observed in almost all parts of the left lower leg on day 7, and the blood flow of the same level as in the untreated right lower leg was observed on day 14 and day 21. In groups (B) and (C), the blood started to flow from day 7, but the blood flow did not recover to the same level as in the right lower leg even when 21 days had passed.

Example 3

Quantification of Blood Flow in Ischemia Model Mouse

The left lower leg ischemia model mice in 4 groups of (A) shCont+PEG-PAsp(DET), (B) naked shPHD2, (C) shPHD2+ PEG-PLL, and (D) shPHD2+PEG-PAsp(DET), that had been treated as shown in Example 1, were measured for the blood flow. Specifically, using a laser Doppler blood flow meter (moorLDI Laser Doppler Imager, Moor Instruments Ltd., England) and software (MLDI VS.1 S/N 5409, Moor Instruments Ltd., England), the blood flow was measured before treatment, after treatment, day 3, day 7, day 14, day 21. The measurement values were quantified to determine the ratio of the ischemia lower leg blood flow to the control lower leg blood flow by using an unoperated right lower leg of the same mouse as a control, and the average value and standard deviation of the blood flow ratio in each group were calculated. The results of (A), (B), (D) are shown in the graph of FIG. 3 *a* and the results of (A), (C), (D) are shown in the graph of FIG. 3 *b*.

Figure 3A:
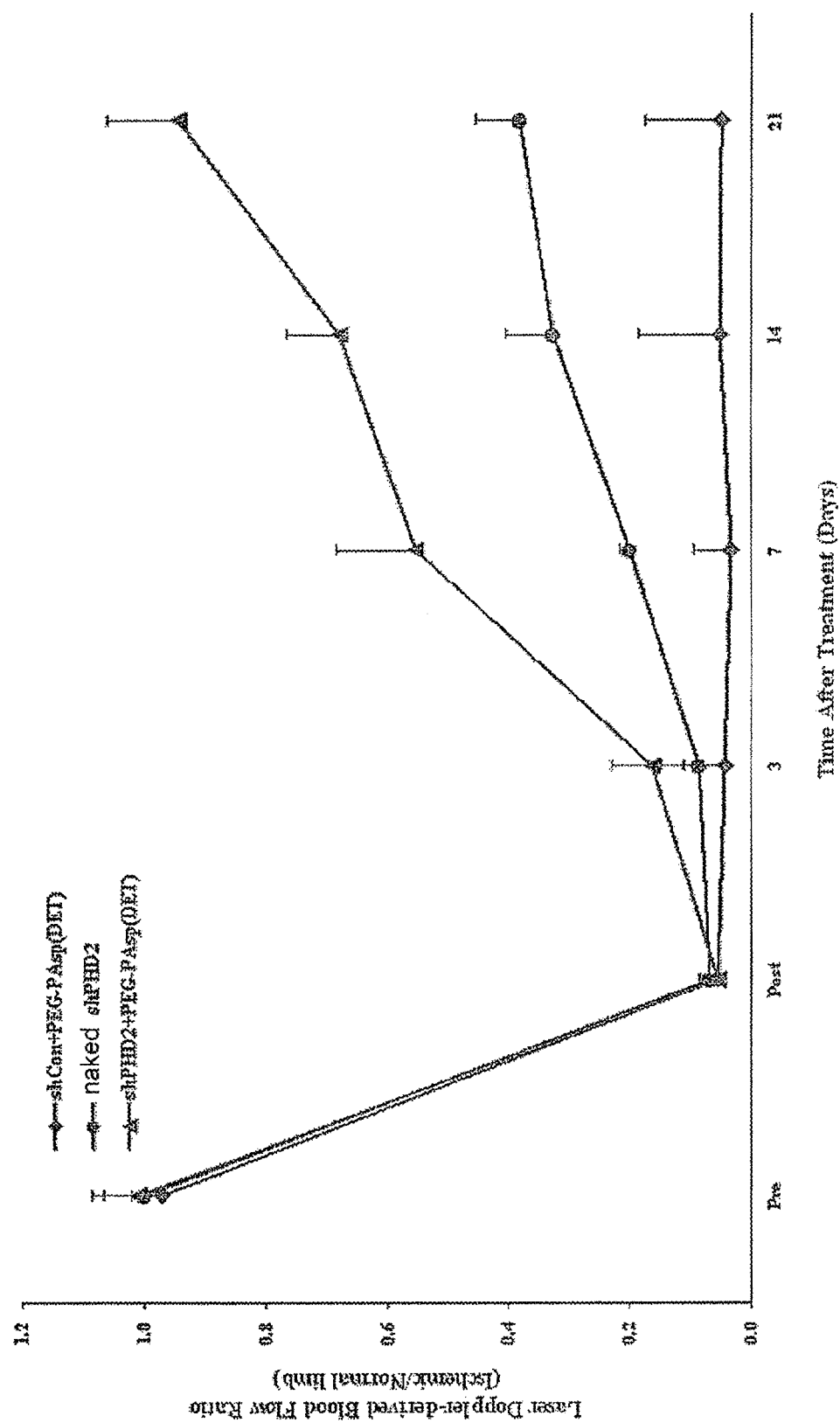
FIG. 3a shows the blood flow quantitative values of lower legs of mouse before an ischemia treatment and thereafter. The blood flow quantitative value shows a ratio of blood flow measurement value of the treated lower legs to that of the untreated lower legs, and shows average values thereof and standard deviation. As test samples, a rhombus mark means use of a polyion complex containing PEG-PAsp (DET) and shRNA expression plasmid (control), a circle means use of only shRNA expression plasmid of PHD2, and a triangle means use of a polyion complex containing PEG-PAsp(DET) and shRNA expression plasmid of PHD2.
Figure 3B:
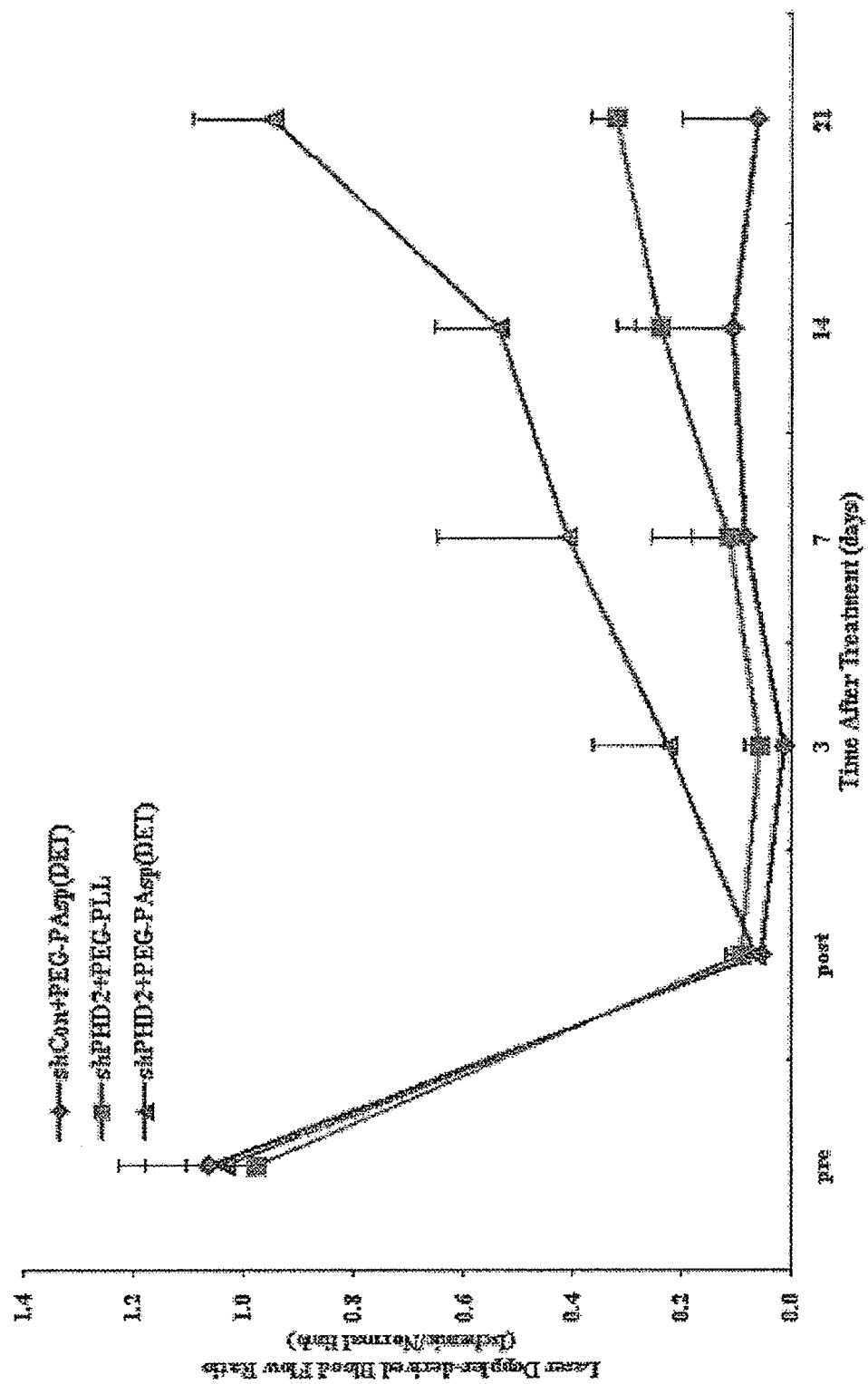
FIG. 3b also shows the blood flow quantitative values of lower legs of mouse, as in FIG. 3a. As test samples, a rhombus mark means use of a polyion complex containing PEG-PAsp (DET) and shRNA expression plasmid (control), a rectangle means use of a polyion complex containing PEG-PLL and shRNA expression plasmid of PHD2, and a triangle means use of a polyion complex containing PEG-PAsp(DET) and shRNA expression plasmid of PHD2.

From the results of FIG. 3 *a*, the mice in group (D) showed, on day 3, a blood flow amount higher than that immediately after the treatment, and the level thereof increased over time to be almost the same level on day 21 as that before the treatment. In contrast, the mice in group (B) showed a blood flow increase over time, but the blood flow amount was lower than that in group (D). In group (A), the blood flow amount did not increase with the progression of time. From the results of FIG. 3 *b*, the mice in group (C) showed a higher amount of blood flow than group (A), though not as high as group (D).

Example 4

Angiogenesis in Ischemia Model Mouse

The left lower leg ischemia model mice in 3 groups of (A) shCont+PEG-PAsp(DET), (B) naked shPHD2, and (D) shPHD2+PEG-PAsp(DET), that had been treated as shown in Example 1, were evaluated by angiography of the mouse lower leg on day 21 after the treatment. For angiography, a catheter was inserted into the region of origin of the descending aorta, a contrast agent (distilled water 50 ml, gelatin (Wako Pure Chemical Industries, Ltd., 1.5 g), lead oxide (Wako Pure Chemical Industries, Ltd., 100 g) was injected, and photographs were taken by an X-ray equipment (SOFTEX CMB-2, Softex Co., Ltd., photographing conditions: 50 V, 22 kVp, 40 sec) and evaluated. The representative photographs of mouse lower leg in each group are shown in FIG. 4, in which an "asterisk (*)" shows the position of ligated external iliac artery, and an arrow shows a newly-formed collateral vessel.

Figure 4:
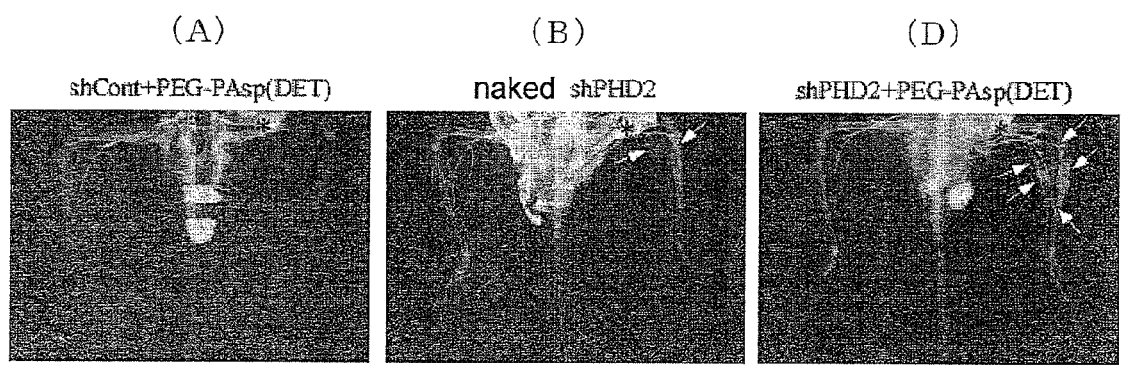
FIG. 4 shows the condition of blood vessels of the mouse lower legs on Day 21 after the ischemia treatment, in which (A) shows administration of shRNA expression plasmid (control) by using PEG-PAsp(DET), (B) shows administration of shRNA expression plasmid of PHD2 without using a polycation chargeable polymer, and (D) shows administration of shRNA expression plasmid of PHD2 by using PEG-PAsp(DET). The position of tied external iliac artery is shown with an asterisk, and the newly formed collateral vessel is shown with an arrow.

As shown in the photographs of FIG. 4, the mice of group (A) did not show a collateral vessel at all, group (B) showed collateral vessel in 2 spots, and group (D) showed collateral vessel in 5 spots.

Example 5

Quantification of PHD2 mRNA Expression

Figure 5:
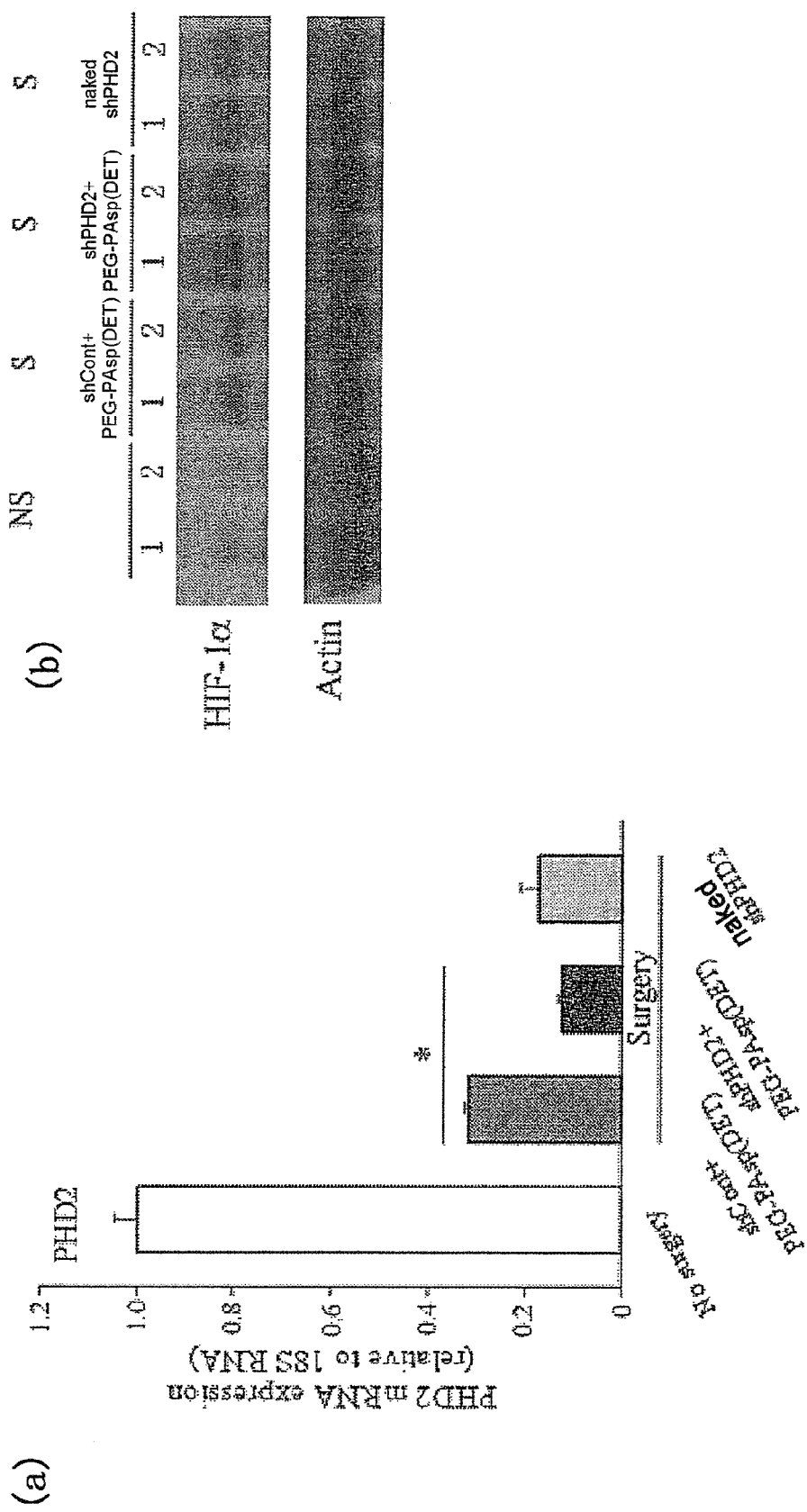
FIG. 5 shows measured expressions of PHD2 and HIF-1α, in which (a) shows the expression amount of PHD2 mRNA in untreated mice and mice administered with various test samples after the ischemia treatment, and (b) shows the results of western blotting relating to HIF-1α expressed in these mice.

The left lower leg ischemia model mice in 3 groups of (A) shCont+PEG-PAsp(DET), (B) naked shPHD2, and (D) shPHD2+PEG-PAsp(DET), that had been treated as shown in Example 1, were each subjected to muscle excision on day 3 after the treatment. Total RNA sample was isolated from the excised muscle by using RNeasy Mini Kit (250) (manufactured by QIAGEN) and RNeasy column (manufactured by QIAGEN) and according to the attached protocol. The isolated RNA sample was subjected to quantitative RT-PCR by using ABI 7500 Fast real-time RT-PCR system (manufactured by Applied Biosystems) and QuantiTect SYBR Green PCR Master Mix (manufactured by QIAGEN) and according to the attached protocol, with PHD2 mRNA as a target. As for the mRNA expression level of each sample, a relative value to mRNA expression level was calculated with 18S rRNA as an internal control. The results are shown in FIG. 5(a). The quantitative RT-PCR was performed using primers having the following base sequences:

```
(mouse PHD2-Forward)
                                    (SEQ ID NO: 5)
5'-GAAGCTGGGCAACTACAGGA-3'
and (mouse PHD2-Reverse)
                                    (SEQ ID NO: 6)
5'-CATGTCACGCATCTTCCATC-3', (18S-Forward)
                                    (SEQ ID NO: 7)
5'-CGGCGACGACCCATTCGAAC-3'
and (18S-Reverse)
                                    (SEQ ID NO: 8)
5'-GAATCGAACCCTGATTCCCGTC-3',
``` and under the temperature and time conditions of carry over step (50° C., 2 min.), PCR initial activation step (95° C., 15 min.), cycle step ([94° C., 15 sec], [60° C., 30 sec], [72° C., 35 sec], cycle number: 40). In FIG. 5(a), "*" means that a statistically significant difference is present (p<0.05).

The left lower leg ischemia model mice in 3 groups of (A), (B) and (D) were each subjected to muscle excision in the same manner on day 7 after the treatment. RIPA buffer (10 µg/ml, aprotinin, 1 mM Na$_3$VO$_4$, 10 mM NaF, protease inhibitor cocktail) was added to the excised muscle, and the mixture was homogenized by a sample precise grinding machine (Multi-beads shocker, Yasui Kikai Corporation) at 2500 rpm for 20 sec and ultracentrifuged at 14000 rpm for 20 sec. The supernatant was recovered as a cell-containing sample. The protein was extracted from the recovered cell-containing sample by using RIPA buffer, after which SDS-PAGE electrophoresis was performed. After transcription onto a PVDF membrane (manufactured by Bio-Rad), western blotting was performed by a conventional method. In this case, anti-mouse HIF-1α antibody (NB100-449; manufactured by Novus Biologicals) was used as the antibody. As the control, actin (manufactured by Sigma Aldrich) was used. The results are shown in FIG. 5(b). The "*" means that a statistically significant difference is present (p<0.05).

As shown in the results of FIG. 5(a), the treated mice in group (D) (shPHD2+PEG-PAsp(DET)) showed a lower PHD2 mRNA expression level than group (A) (shCont+PEG-PAsp(DET)) and group (B) (naked shPHD2), exhibiting a statistically significant difference from the mRNA expression level of group (A).

The results of FIG. 5(b) reveal that all the treated mice showed HIF-1α, and HIF-1α was induced most in the mice of group (D) (shPHD2+PEG-PAsp(DET)).

Example 6

Quantification of Angiogenesis Factor mRNA Expression

Figure 6:
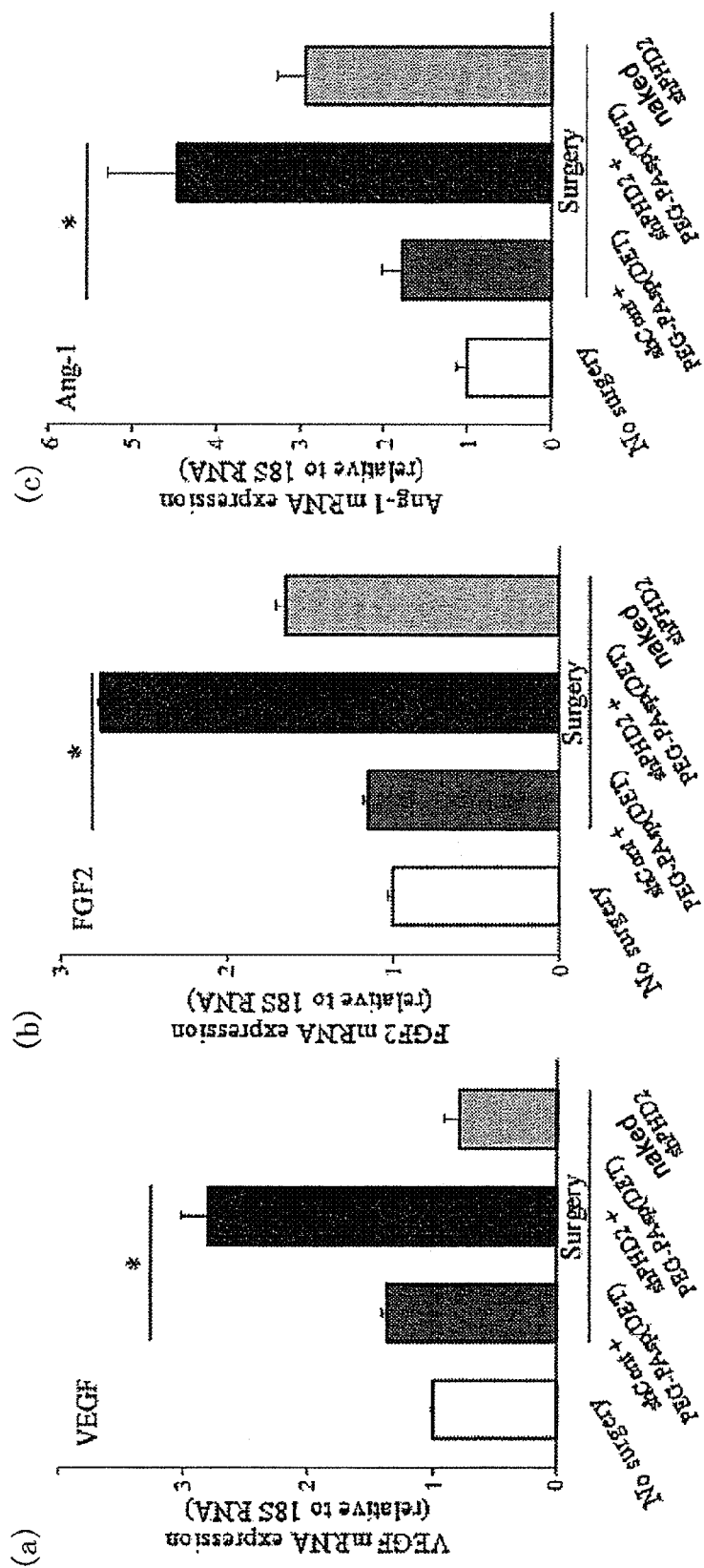
FIG. 6 shows measured expressions of VEGF, FGF2 and Ang-1, in which (a) shows the expression amount of VEGF mRNA in untreated mice and mice administered with various test samples after the ischemia treatment, (b) shows the expression amount of FGF2 mRNA expression in these mice, and (c) shows the expression amount of Ang-1 mRNA in these mice.

RNA samples were isolated from the left lower leg muscle of the left lower leg ischemia model mice in 3 groups of (A), (B) and (D) on day 3 after the treatment, in the same manner as in Example 5, and quantitative RT-PCR was performed using (a) VEGF, (b) FGF2 and (c) Ang-1 as targets. Quantitative RT-PCR was performed using primers having the following base sequences:

```
(VEGF-Forward)
                                    (SEQ ID NO: 9)
5'-GCAGAAGTCCCATGAAGTGAT-3'
and (VEGF-Reverse)
                                    (SEQ ID NO: 10)
5'-GTCTCAATTGGACGGCAGTAG-3', (FGF2-Forward)
                                    (SEQ ID NO: 11)
5'-GTCACGGAAATACTCCAGTTGGT-3'
and (FGF2-Reverse)
                                    (SEQ ID NO: 12)
5'-CCCGTTTTGGATCCGAGTT-3', (Ang1-Forward)
                                    (SEQ ID NO: 13)
5'-TTGTGATTCTGGTGATTGTGG-3'
and (Ang1-Reverse)
                                    (SEQ ID NO: 14)
5'-CTTGTTTCGCTTTATTTTTGT-3',
``` with other conditions the same as in Example 5, and the relative value to the mRNA expression level of the internal control 18S rRNA was calculated. The results are shown in FIG. 6(a)-(c). The "*" means that a statistically significant difference is present (p<0.05).

As shown in the results of FIG. 6(a)-(c), among the treated mice, the mice of group (D) (shPHD2+PEG-PAsp(DET)) showed the highest mRNA expression level for all of (a) VEGF, (b) FGF2 and (c) Ang-1. In addition, a statistically significant difference was observed in any of (a)-(c) from the mRNA expression level of the mice of group (A).

Industrial Applicability

According to the present invention, angiogenesis can be induced directly or indirectly via stabilization of HIF (HIF-1 or HIF-2), which can realize quantitatively and functionally superior regeneration of blood vessels and can provide a pharmaceutical product effective for the treatment or prophylaxis of ischemic diseases, arterial diseases and the like.

This application is based on patent application No. 2009-171562 filed in Japan (filing date: Jul. 22, 2009), the contents of which are encompassed in full herein.

The invention claimed is:

1. A pharmaceutical composition comprising, a polyion complex comprising a polyanionic substance as an active ingredient that suppresses the expression of PHD2, a polycation chargeable polymer, and glycosaminoglycan, which forms a ternary system complex of the polyion complex and glycosaminoglycan, wherein the polyanionic substance is selected from the group consisting of RNAi inducing nucleic acid against PHD2 or an expression vector thereof, antisense nucleic acid against PHD2 or an expression vector thereof, and a ribozyme against PHD2 or an expression vector thereof, and the polycation chargeable polymer is a chargeable polymer represented by the following formula (III), a block copolymer represented by the following formula (I) or (II), or a salt thereof,

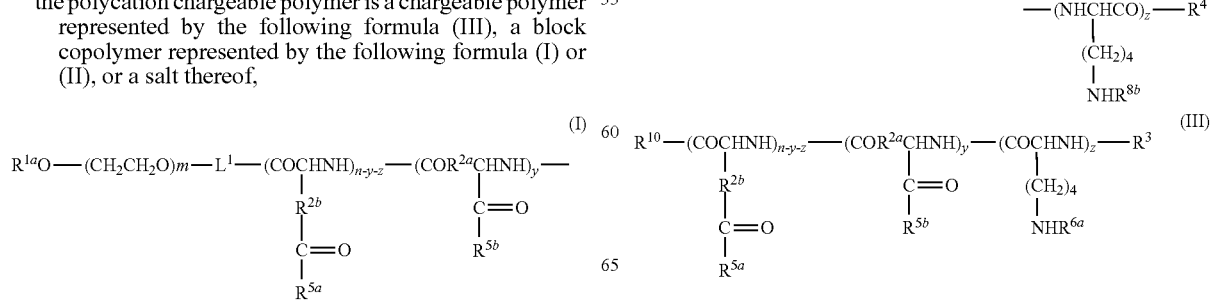

wherein,

R¹⁰ is a hydroxy group, an oxybenzyl group or an NH—R¹¹ group, wherein R¹¹ is an optionally substituted straight chain or branched $C_{1-20}$ alkyl group, $R^{1a}$ and $R^{1b}$ are each independently a hydrogen atom or an optionally substituted straight chain or branched $C_{1-12}$ alkyl group, $R^{2a}$, $R^{2b}$, $R^{2c}$ and $R^{2d}$ are each independently a methylene group or an ethylene group, $R^3$ is a hydrogen atom, a protecting group, a hydrophobic group or a polymerizable group, $R^4$ is a hydroxy group, a protecting group or a group represented by —O—X³, —S—X³, —NH—X³, or a polymerization initiator residue of polypeptide, wherein X³ is a primary, secondary or tertiary amine compound, or an amine compound residue comprising one or more groups derived from a quaternary ammonium salt, or a non-amine compound residue, $R^{5a}$, $R^{5b}$, $R^{5c}$ and $R^{5d}$ are each independently a hydroxy group, an oxybenzyl group or an NH—(CH₂)ₐ—X group, wherein a is an integer of 1-5, X is each independently a primary, secondary or tertiary amine compound, or an amine compound residue comprising one or more groups derived from a quaternary ammonium salt, or a non-amine compound residue, the total of $R^{5a}$ and $R^{5b}$ or $R^{5c}$ and $R^{5d}$ contains at least two —NH—(CH₂)ₐ—X¹ groups (wherein X¹ is (NH(CH₂)₂)ₑ—NH₂, and e is an integer of 1-5), $R^{6a}$ and $R^{6b}$ are each independently a hydrogen atom or protecting group, wherein the protecting group is selected from the group consisting of a Z group, a Boc group, an acetyl group and a trifluoroacetyl group, L¹ and L² are linking groups, m is an integer of 5-20,000, n is an integer of 2-5,000, y is an integer of 0-5,000, z is an integer of 0-5,000, and y+z is not larger than n, and each repeat unit in the above formulas may be present in the above specified order or may be present in a random order.

2. The pharmaceutical composition according to claim 1, wherein the RNAi inducing nucleic acid is siRNA or an expression vector thereof.

3. The pharmaceutical composition according to claim 1, wherein X is a group selected from the group consisting of —NH₂, —NH—CH₃, —N(CH₃)₂ and groups represented by the following formulas:

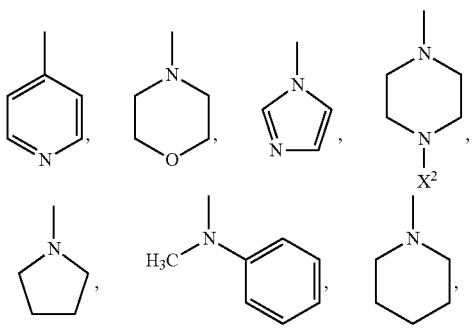

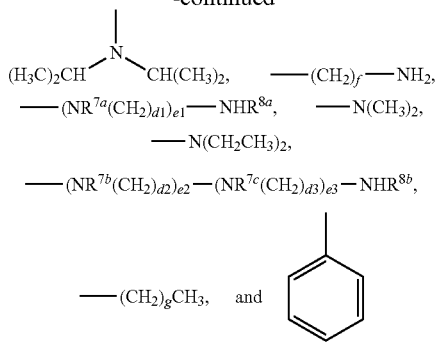

wherein,

X² is a hydrogen atom, a $C_{1-6}$ alkyl group or an amino $C_{1-6}$ alkyl group, $R^{7a}$, $R^{7b}$ and $R^{7c}$ are each independently a hydrogen atom or a methyl group, d1, d2 and d3 are each independently an integer of 1-5, e1, e2 and e3 are each independently an integer of 1-5, f is an integer of 0-15, $R^{8a}$ and $R^{8b}$ are each independently a hydrogen atom or a protecting group, wherein the protecting group is selected from the group consisting of a Z group, a Boc group, an acetyl group and a trifluoroacetyl group, and g is an integer of 0-15.

4. The pharmaceutical composition according to claim 1, wherein L¹ or L² has a disulfide bond.

5. The pharmaceutical composition according to claim 1, wherein the glycosaminoglycan is chondroitin sulfate or a salt thereof.

6. The pharmaceutical composition according to claim 1, which is for the treatment or prophylaxis of an ischemic disease or artery disease.

7. The pharmaceutical composition according to claim 6, wherein the ischemic disease or artery disease is selected from the group consisting of ischemic cardiac disease, myocardial infarction, cardiomyopathy, angina pectoris, unstable angina pectoris, coronary sclerosis, cardiac failure, arteriosclerosis obliterans, Buerger's disease, vascular injury, artery obstruction, arterial thrombosis, organ artery obstruction, aneurysm, ischemic brain diseases, ischemic lung disease and renal infarction.

8. A method for the treatment or prophylaxis of an ischemic disease or artery disease, comprising a step of administering the pharmaceutical composition according to claim 1 to a subject in need thereof.

9. The method for the treatment or prophylaxis according to claim 8, wherein the ischemic disease or artery disease is selected from the group consisting of ischemic cardiac disease, myocardial infarction, cardiomyopathy, angina pectoris, unstable angina pectoris, coronary sclerosis, cardiac failure, arteriosclerosis obliterans, Buerger's disease, vascular injury, artery obstruction, arterial thrombosis, organ artery obstruction, aneurysm, ischemic brain disease, ischemic lung disease and renal infarction.

* * * * *